US012636178B2

(12) United States Patent
Finley

(10) Patent No.: US 12,636,178 B2
(45) Date of Patent: May 26, 2026

(54) LOWER EXTREMITY ORTHOSES DEVICES

(71) Applicant: Ulcer Solutions, LLC, Ridgefield, WA (US)

(72) Inventor: Christopher J. Finley, Ridgefield, WA (US)

(73) Assignee: ULCER SOLUTIONS, LLC, Ridgefield, WA (US)

( * ) Notice: Subject to any disclaimer, the term of this patent is extended or adjusted under 35 U.S.C. 154(b) by 934 days.

(21) Appl. No.: 17/682,086

(22) Filed: Feb. 28, 2022

(65) Prior Publication Data

US 2023/0270578 A1 Aug. 31, 2023

(51) Int. Cl.
*A61F 13/00* (2024.01)
*A61F 5/01* (2006.01)
(52) U.S. Cl.
CPC .... *A61F 5/0195* (2013.01); *A61F 2005/0167* (2013.01); *A61F 2005/0172* (2013.01)
(58) Field of Classification Search
CPC ............................. A61F 5/0195; A61F 5/0127
USPC ........................................................ 602/27
See application file for complete search history.

(56) References Cited

U.S. PATENT DOCUMENTS

| | | | |
|---|---|---|---|
| 3,345,654 A | 10/1967 | Noble | |
| 3,946,451 A | 3/1976 | Spann | |
| 4,076,022 A | 2/1978 | Walker | |
| 4,104,746 A | 8/1978 | Goetz | |

| | | | |
|---|---|---|---|
| 4,186,738 A | 2/1980 | Schleicher et al. | |
| 4,266,298 A | 5/1981 | Graziano | |
| 4,573,456 A | 3/1986 | Spann | |
| 4,616,639 A | 10/1986 | Huber | |

(Continued)

FOREIGN PATENT DOCUMENTS

| | | |
|---|---|---|
| CN | 218739416 U | 3/2023 |
| CN | 219662139 U | 9/2023 |

(Continued)

OTHER PUBLICATIONS

Amazon.com, "Comfy Boot Splint, Adult" product page, https://www.amazon.com/Comfy-Boot-Splint-Adult/dp/B00A29WN4A (Jul. 13, 2023).

(Continued)

*Primary Examiner* — Kim M Lewis
(74) *Attorney, Agent, or Firm* — Vitruvian IP Law LLC; Cecily Anne O'Regan; Jeong Hee Seo

(57) ABSTRACT

A lower extremity orthosis includes a foot engagement portion and an elongated positioning member. The foot engagement portion is configured to engage a patient's foot and includes opposing sidewalls extending from a sole-supporting surface configured to engage with a sole of the patient's foot. The elongated positioning member includes a foot-underlying portion and a lower leg-underlying portion, with the foot-underlying portion of the elongated positioning member serving to couple the elongated positioning member to the foot engagement portion. The lower extremity orthosis may be selectively and removably engaged with a heel offloading device via the lower leg-underlying portion of the elongated positioning member, such that the lower extremity orthosis is configured to prevent or reduce plantar flexion when the heel offloading device is used and the lower extremity orthosis is applied to the patient's foot.

17 Claims, 13 Drawing Sheets

(56) References Cited

U.S. PATENT DOCUMENTS

| | | | |
|---|---|---|---|
| 5,328,445 | A | 7/1994 | Spahn et al. |
| 5,336,160 | A * | 8/1994 | Christensen ............ A61F 5/055 |
| | | | 602/18 |
| 5,449,339 | A | 9/1995 | Drennan |
| 5,569,173 | A | 10/1996 | Varn |
| 5,603,690 | A | 2/1997 | Barry |
| 5,665,059 | A | 9/1997 | Klearman et al. |
| 5,762,622 | A * | 6/1998 | Lamont ................ A61F 5/0127 |
| | | | 602/65 |
| 5,957,872 | A | 9/1999 | Flick |
| 5,957,874 | A | 9/1999 | Klein |
| 5,997,491 | A | 12/1999 | Harris |
| 6,149,613 | A | 11/2000 | Klein |
| 6,468,239 | B1 | 10/2002 | Mollura, Sr. et al. |
| 6,572,573 | B1 | 6/2003 | Klein |
| 6,793,640 | B1 | 9/2004 | Avon |
| 7,112,180 | B2 * | 9/2006 | Guenther .............. A61F 5/0111 |
| | | | 602/29 |
| 7,188,382 | B1 | 3/2007 | Taylor et al. |
| 7,458,948 | B2 | 12/2008 | Drennan |
| 7,798,984 | B2 | 9/2010 | Ponsi et al. |
| 7,909,787 | B2 | 3/2011 | Ravikumar |
| 7,967,788 | B2 | 6/2011 | Chandrasekar et al. |
| 8,070,701 | B2 | 12/2011 | Flam et al. |
| 9,339,405 | B2 | 5/2016 | Eriksson et al. |
| 9,392,874 | B2 | 7/2016 | Shaffer |
| 9,615,958 | B2 | 4/2017 | Davis et al. |
| 9,980,845 | B2 | 5/2018 | Drey et al. |
| 10,334,905 | B2 | 7/2019 | Drennan |
| 11,259,950 | B1 | 3/2022 | Finley |
| 2001/0016960 | A1 | 8/2001 | Grabell et al. |
| 2002/0032485 | A1 | 3/2002 | Flam et al. |
| 2003/0032908 | A1 | 2/2003 | Nayfa |
| 2003/0191420 | A1 | 10/2003 | Kuiper et al. |
| 2004/0092853 | A1 | 5/2004 | Degun et al. |
| 2005/0107728 | A1 | 5/2005 | Vetters et al. |
| 2005/0203451 | A1 | 9/2005 | Reis et al. |
| 2006/0241541 | A1 | 10/2006 | Ravikumar |
| 2007/0074427 | A1 * | 4/2007 | Ponsi .................... A61F 5/0111 |
| | | | 36/110 |
| 2007/0095353 | A1 | 5/2007 | Ravikumar |
| 2012/0145167 | A1 * | 6/2012 | Davis .................... A61F 5/0111 |
| | | | 128/882 |
| 2012/0199134 | A1 | 8/2012 | Carson |
| 2013/0319426 | A1 | 12/2013 | Castle |
| 2015/0018740 | A1 | 1/2015 | Davis et al. |
| 2015/0019740 | A1 | 1/2015 | Davis et al. |
| 2016/0256329 | A1 * | 9/2016 | Spahn .................. A61F 5/0111 |
| 2016/0279006 | A1 | 9/2016 | Crewdson |
| 2018/0014963 | A1 | 1/2018 | Griffiths et al. |
| 2018/0153729 | A1 | 6/2018 | Ponsi et al. |
| 2018/0214295 | A1 | 8/2018 | Davis |
| 2019/0216665 | A1 | 7/2019 | Miller et al. |
| 2022/0054291 | A1 | 2/2022 | Huber |

FOREIGN PATENT DOCUMENTS

| | | |
|---|---|---|
| SE | 517788 C2 | 7/2002 |
| SE | 517788 | 7/2022 |
| WO | 2007101289 A1 | 9/2007 |
| WO | 2014154499 A1 | 10/2014 |
| WO | WO 2014154499 | 10/2014 |
| WO | 2023163867 A1 | 8/2023 |

OTHER PUBLICATIONS

Youtube.com, "DeRoyal® Ankle Contracture Boot," Rehabmart Reviews, https://www.youtube.com/watch?v=u1xwx6v6DDE (Oct. 4, 2013).

Ulcer Solutions Heel Keeper, product information downloaded from www.ulcersolutions.com/product/heel-keeper/, available at least as early as May 14, 2019.

Performance Health Heelift AFO, product information downloaded from www.performancehealth.ca/heelift-afo on Apr. 20, 2021.

Walgreen Health Solutions, Heelift AFO Application and Fitting Guide, 2021.

English translation of the Abstract of Swedish Patent No. SE517788, Jul. 16, 2002.

* cited by examiner

LOWER EXTREMITY ORTHOSES DEVICES

FIELD

The present disclosure relates generally to lower extremity orthoses and systems including the same, and more particularly to orthoses configured to be selectively engaged with heel offloading devices to prevent plantar flexion when the heel offloading device is used.

BACKGROUND

Many patients spend long hours on bedrest during recovery from various forms of trauma, accidents, or illnesses. During this prolonged bedrest, patients can develop what are commonly known as bedsores, or pressure ulcers. Such pressure ulcers are particularly common in the heel region, due to anatomical characteristics of the heel region (e.g., thin skin in the area, and little by way of underlying soft tissue or muscle overlying a bony prominence), combined with pressure, shear forces, and/or friction forces from positioning of the immobilized patient. For example, when the head of the bed is elevated (which is often performed to improve the patient's comfort and/or respiratory functions), such movement may increase pressure on the heel and/or create a sliding movement of the patient's heel along the bed surface, thereby creating shear forces. Internal shear stresses and strains also may be caused by bone and connective tissue movement relative to the skin, such as due to friction between the heel and the bed surface.

Devices for preventing, treating, and/or healing bedsores in the heel region of the patient have been developed that offload the heel, thereby reducing or eliminating contact between the patient's heel and the bed or other surfaces. This may be accomplished simply by using a pillow or cushion underneath the calf. However, a simple pillow or cushion often fails to maintain the position of the heel, with the heel easily slipping off the pillow, which can exacerbate pressure and/or friction on the heel. Heel offloading boot-like devices (often referred to simply as "boots") have been developed to offload the heel, though some such devices suffer from low patient compliance, as they may be hot, bulky, uncomfortable, and/or prone to displacement. Such devices also may limit the patient's ability to move their leg or change positions while in bed, and/or may not be suitable for ambulation while wearing the device (e.g., the devices may be difficult or unsafe to walk in, due to an increased fall risk). Furthermore, patients may experience plantar flexion and/or contractures while wearing various devices that elevate the patient's lower legs to offload the heel, which can create further difficulties for the patient, such as plantar flexion contracture (stiff ankle joint with the foot in a plantar flexion position which prevents ambulation; sometimes referred to as "drop foot") and/or other difficulties with walking or moving around after they are off bedrest.

SUMMARY

Presently disclosed lower extremity orthoses may include a foot engagement portion configured to engage a patient's foot, and an elongated positioning member comprising a foot-underlying portion and a lower leg-underlying portion. The foot engagement portion may include opposing sidewalls extending from a sole-supporting surface configured to engage with a sole of the patient's foot. The foot-underlying portion of the elongated positioning member may be configured to couple the elongated positioning member to the foot engagement portion. Such disclosed lower extremity orthoses may be configured to be selectively and removably engaged with a heel offloading device via the lower leg-underlying portion of the elongated positioning member, such that the lower extremity orthosis may be configured to prevent or reduce plantar flexion when the heel offloading device is used and the lower extremity orthosis is applied to the patient's foot.

Presently disclosed systems may include a lower extremity orthosis and a heel offloading device, with the lower extremity orthosis being configured to be selectively and removably engaged with the heel offloading device via the lower leg-underlying portion of the elongated positioning member, such that the lower extremity orthosis is configured to prevent or reduce plantar flexion when the heel offloading device is used and the lower extremity orthosis is applied to the patient's foot. Such heel offloading devices may include a concave member extending from a first end to a second end, the first end being configured to engage the patient's lower leg superior to the patient's ankle, and the second end being configured to engage the lower leg at or inferior to the patient's mid-calf. The heel offloading device also may include a first and second sidewall projecting from a floor of the concave member. Interior portions of the first and second sidewalls and the floor together may define a lower leg-receiving surface that is configured to embrace the patient's lower leg when the heel offloading device is worn by the patient.

DESCRIPTION

Figures 1, 1A, 1B:
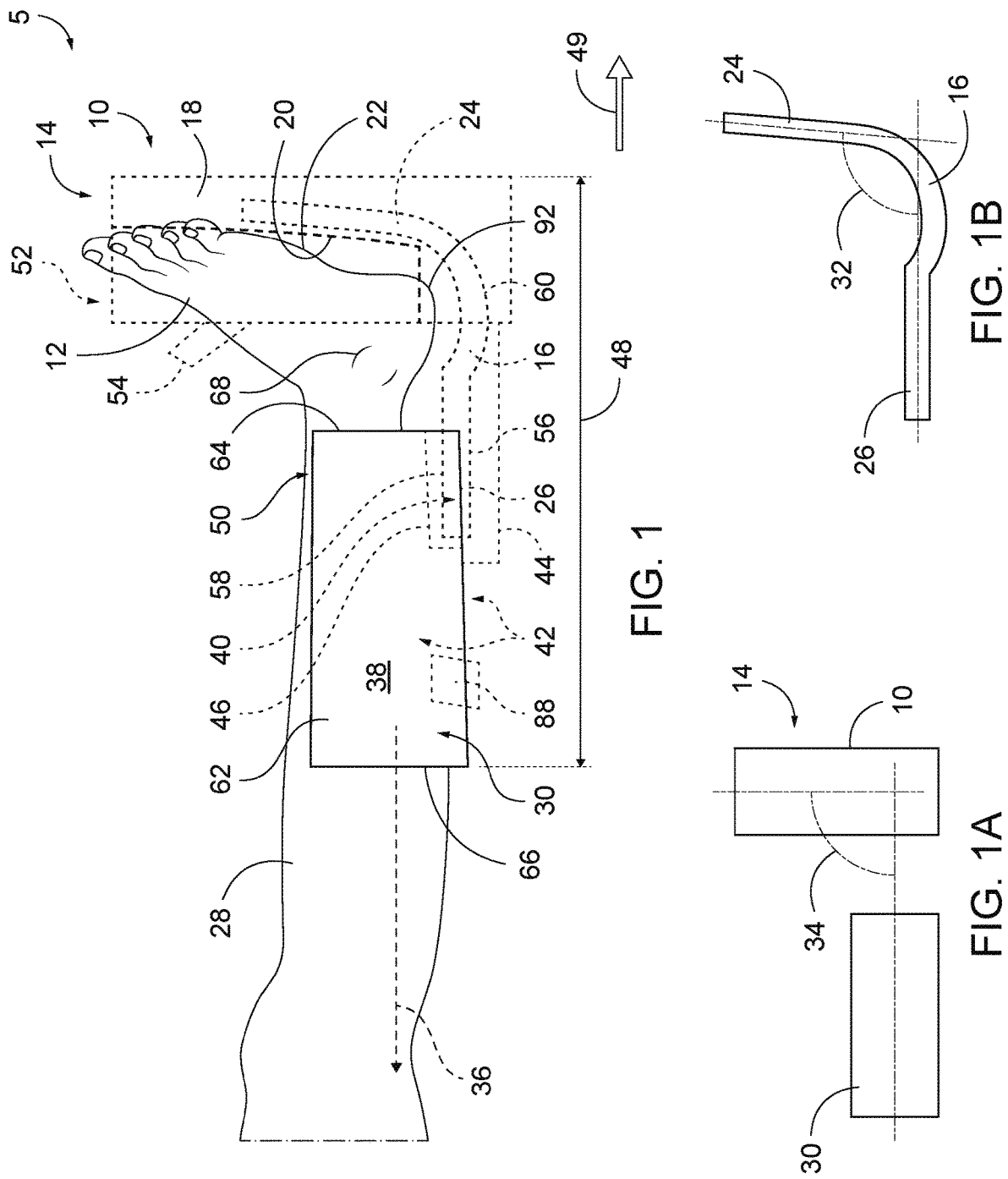
FIG. 1 is a schematic, side elevation representation of illustrative, non-exclusive examples of systems according to the present disclosure.
FIG. 1A is a schematic representation of an arrangement between a lower extremity orthosis according to the present disclosure and a heel offloading device.
FIG. 1B is a schematic representation of an angle formed by an elongated positioning member of presently disclosed lower extremity orthoses.
Figure 2:
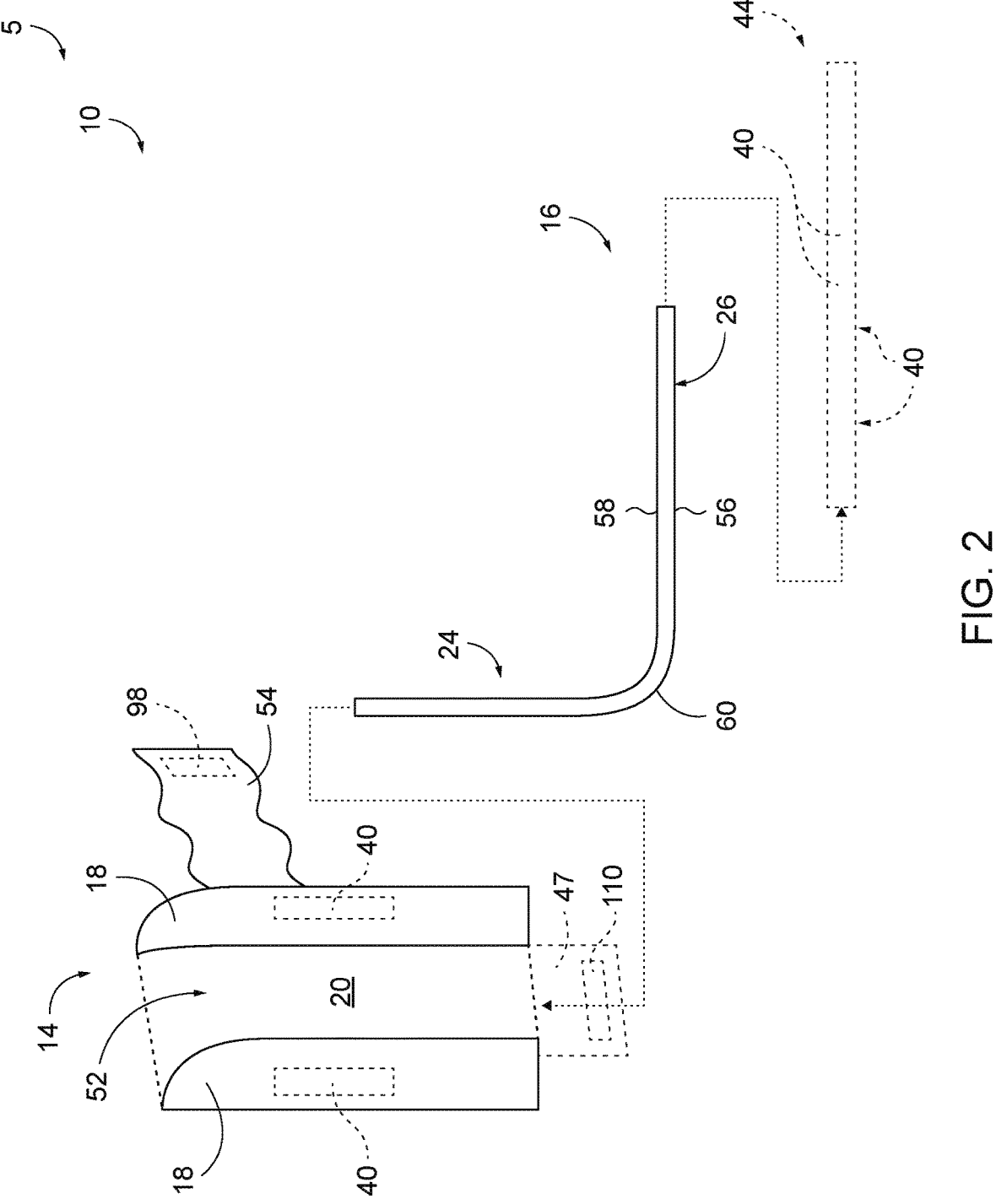
FIG. 2 is an exploded, schematic black box representation of illustrative non-exclusive examples of lower extremity orthoses according to the present disclosure.
Figure 3:
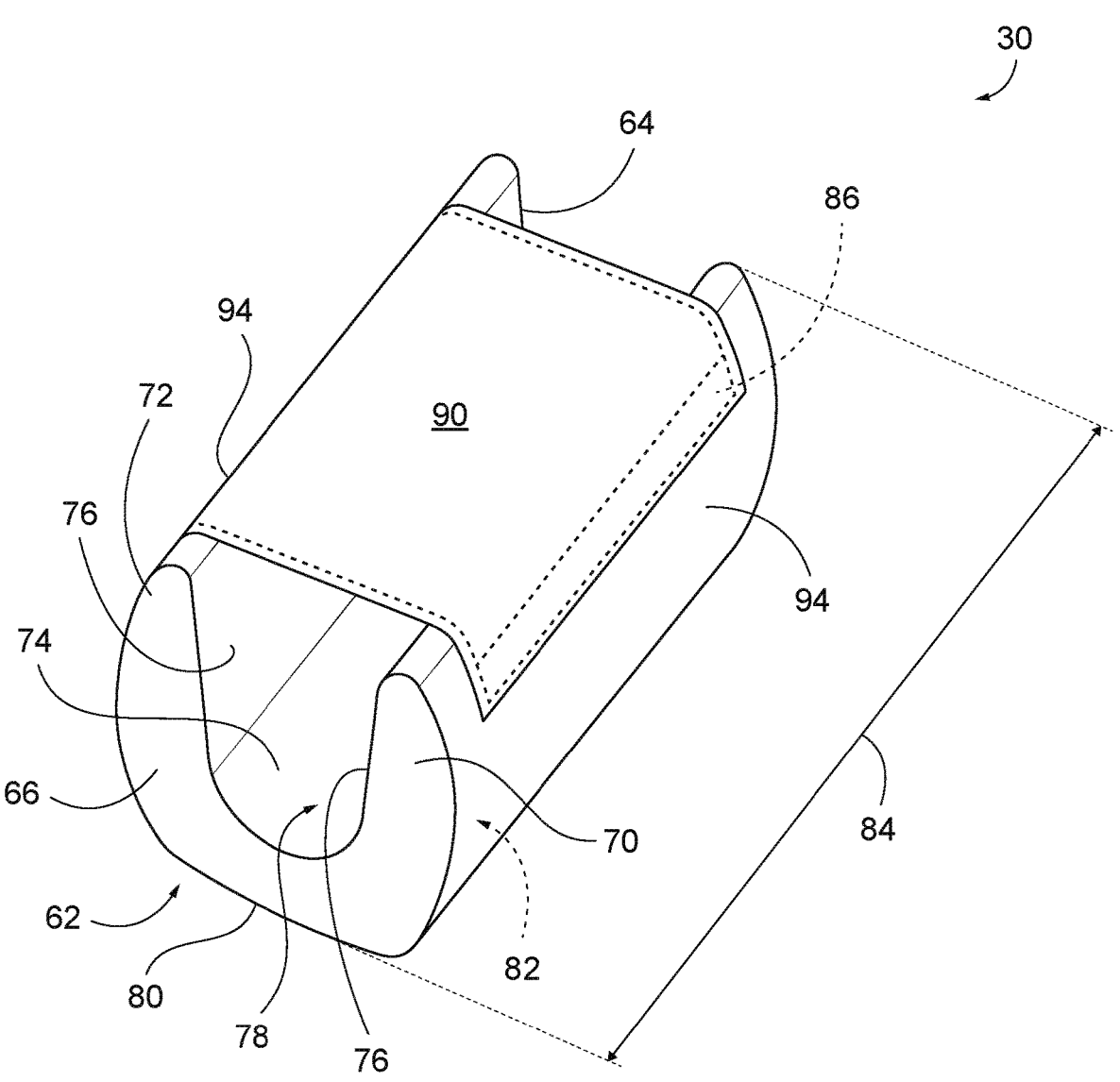
FIG. 3 is a schematic representation of illustrative, non-exclusive examples of heel offloading devices that may be used with presently disclosed lower extremity orthoses.

FIGS. 1-3 provide illustrative, non-exclusive examples of lower extremity orthosis 10 and/or heel offloading device 30 according to the present disclosure. Elements that serve a similar, or at least substantially similar, purpose are labeled with like numbers in each of FIGS. 1-3, and these elements may not be discussed in detail herein with reference to each of FIGS. 1-3. Similarly, all elements may not be labeled in each of FIGS. 1-3, but reference numerals associated therewith may be utilized herein for consistency. Elements, components, and/or features that are discussed herein with reference to one or more of FIGS. 1-3 may be included in and/or utilized with any of FIGS. 1-3 without departing from the scope of the present disclosure. In general, elements that are likely to be included in a given (i.e., a particular) example are illustrated in solid lines, while elements that are optional to a given example are illustrated in dashed lines. However, elements that are shown in solid lines are not essential to all examples, and an element shown in solid lines may be omitted from a particular example without departing from the scope of the present disclosure.

FIGS. 1-2 schematically represent non-exclusive examples of disclosed lower extremity orthoses 10 according to the present disclosure, shown in the context of systems 5 that include lower extremity orthosis 10 and a heel offloading device 30, though in various examples, lower extremity orthosis 10 may be provided without, or separately from, heel offloading device 30. FIG. 1 represents a side view of lower extremity orthosis 10 and heel offloading device 30 in place on a patient's foot 12 and lower leg 28, respectively, while FIG. 2 represents an exploded, schematic black box view of lower extremity orthosis 10 on its own. Lower extremity orthosis 10 includes a foot engagement portion 14 and an elongated positioning member 16. Foot engagement portion 14 is configured to engage foot 12, and may include opposing sidewalls 18 and a sole-supporting surface 20 configured to engage with a sole 22 of foot 12. Elongated positioning member 16 includes a foot-underlying portion 24 and a lower leg-underlying portion 26. As best seen in FIG. 1, foot-underlying portion 24 may be positioned to underlie, or be positioned inferiorly to, at least a portion of sole 22 of foot 12 when lower extremity orthosis 10 is applied to foot 12, while lower leg-underlying portion 26 may underlie at least a portion of the patient's lower leg 28 while lower extremity orthosis 10 is worn (e.g., applied to foot 12). When a patient's foot is secured in foot engagement portion 14, foot-underlying portion 24 of elongated positioning member 16 may be sized and shaped to extend to underlie some or all of the patient's foot, such as the midfoot, forefoot, and/or toes. Foot-underlying portion 24 is configured to couple elongated positioning member 16 to foot engagement portion 14 of lower extremity orthosis 10.

Lower extremity orthosis 10 is configured to be selectively and removably engaged with heel offloading device 30, via lower leg-underlying portion 26 of elongated positioning member 16. Lower extremity orthosis 10 is sized, shaped, and coupled to heel offloading device 30 in such a way that lower extremity orthosis 10 is positioned with respect to foot 12 such that lower extremity orthosis 10 is configured to prevent or reduce plantar flexion of foot 12 when heel offloading device 30 is used while lower extremity orthosis 10 is applied to foot 12. In some examples, foot-underlying portion 24 of elongated positioning member 16 is arranged at a non-parallel and/or non-perpendicular angle with respect to lower leg-underlying portion 26 of elongated positioning member 16. For example, an angle 32 may be defined by the intersection of a first plane defined by lower leg-underlying portion 26 and a second plane defined by foot-underlying portion 24 of elongated positioning member 16, as represented in FIG. 18. In some examples, angle 32 may be less than 70 degrees, less than 75 degrees, less than 80 degrees, less than 85 degrees, less than 90 degrees, less than 95 degrees, less than 100 degrees, less than 105 degrees, and/or less than 110 degrees. Angle 32 may be substantially fixed when in normal use, or angle 32 may be selectively adjustable (e.g., via a hinge, a ratchet, or bending of elongated positioning member 16).

Additionally or alternatively, elongated positioning member 16 may be configured to couple lower extremity orthosis 10 to heel offloading device 30 such that foot engagement portion 14 of lower extremity orthosis 10 maintains a threshold angle 34 with respect to a longitudinal axis 36 of heel offloading device 30 (as represented in FIG. 1A), thereby preventing or reducing plantar flexion of foot 12. In some examples, threshold angle 34 may be less than 70 degrees, less than 75 degrees, less than 80 degrees, less than 85 degrees, less than 90 degrees, less than 95 degrees, less than 100 degrees, less than 105 degrees, and/or less than 110 degrees. Threshold angle 34 may be selectively adjustable in some examples, such as via a hinge or other adjustment mechanism. To create the desired arrangement for the patient's foot with respect to their lower leg, foot-underlying portion 24 of elongated positioning member 16 may be substantially perpendicular to lower leg-underlying portion 26 of elongated positioning member 16 (e.g., angle 32 may be approximately 90 degrees). In other examples, foot-underlying portion 24 may form an acute angle 32 with lower leg-underlying portion 26. In other examples, foot-underlying portion 24 may form an obtuse angle 32 with lower leg-underlying portion 26. In some examples, angle 32 between foot-underlying portion 24 and lower leg-underlying portion 26 may be selectively adjustable, such as by elastic or plastic deformation of elongated positioning member 16, via hinge or joint of elongated positioning member 16, and/or via other adjustment of elongated positioning member 16.

In some examples of system 5, foot-underlying portion 24 is integrally formed with lower leg-underlying portion 26 to form a monolithic body of elongated positioning member 16. Elongated positioning member 16 generally is semi-rigid or rigid, such as being configured to allow some bending of elongated positioning member 16, while still retaining its overall shape to position the patient's foot and prevent or reduce foot drop when lower extremity orthosis 10 is used in conjunction with heel offloading device 30. Elongated positioning member 16 may include a curved heel portion 60 extending between (e.g., positioned between) foot-underlying portion 24 and lower leg-underlying portion 26 of elongated positioning member 16. Curved heel portion 60 may be integrally formed with foot-underlying portion 24 and lower leg-underlying portion 26 as well. Curved heel portion 60 may be configured to prevent or avoid contacting the patient's heel when lower extremity orthosis 10 is used by the patient. For example, curved heel portion 60 may be cupped to create a concavity that is large enough to avoid contacting the patient's heel when the device is worn. In some examples, curved heel portion 60 may be a cut-out formed in elongated positioning member 16, in addition to or instead of the curved area. In this manner, lower extremity orthosis 10 may be configured to be worn by a bedridden or supine patient without counteracting the heel offloading action of heel offloading device 30, yet providing stability to prevent or reduce foot drop while said heel offloading device 30 is used by the patient. In this manner, lower extremity orthosis 10 and heel offloading device 30 are configured to work together to safely and comfortably support the patient's lower leg and foot, to prevent or reduce both pressure ulcers and plantar flexion contracture (e.g., foot drop) in these patients.

In various examples of system 5, lower leg-underlying portion 26 of elongated positioning member 16 may be configured to selectively and removably couple lower extremity orthosis 10 to heel offloading device 30 in any suitable manner. In a representative example, lower leg-underlying portion 26 may couple lower extremity orthosis 10 to heel offloading device 30 via engagement with an outer surface 38 of heel offloading device 30. For example, lower leg-underlying portion 26 may include a first hook and loop fastener 40 configured to couple lower extremity orthosis 10 to heel offloading device 30 via engagement with a second hook and loop fastener 42 of heel offloading device 30 (e.g., second hook and loop fastener 42 may be positioned on or embedded within outer surface 38 of heel offloading device 30). In some specific examples, lower leg-underlying portion 26 may include a sleeve 44 placed on or around lower-leg underlying portion 26 to cover and/or protect patients from edges and surfaces of elongated positioning member 16. Sleeve 44 may be configured to selectively and removably couple lower extremity orthosis 10 to heel offloading device 30. For example, sleeve 44 may include first hook and loop fastener 40. Additionally or alternatively, sleeve 44 may include a fastener configured to selectively and removably couple lower extremity orthosis 10 to heel offloading device 30. Additionally or alternatively, lower leg-underlying portion 26 may be configured to be at least partially inserted into a slot or pocket 46 of heel offloading device 30 to couple lower extremity orthosis 10 to heel offloading device 30. In disclosed examples, lower extremity orthosis 10 is configured to prevent or reduce plantar flexion of foot 12 when lower extremity orthosis 10 is coupled to heel offloading device 30 and both are secured to the patient's foot 12 and leg 28.

In some systems 5, elongated positioning member 16 is selectively removable from foot engagement portion 14. In some examples, the relative position of foot engagement portion 14 along the length of foot-underlying portion 24 may be selectively adjustable by translating foot engagement portion 14 to different positions or locations along the length of foot-underlying portion 24. In other words, foot engagement portion 14 may be selectively translatable with respect to foot-underlying portion 24 of elongated positioning member 16, such as by sliding foot engagement portion 14 along foot-underlying portion 24 to accommodate larger feet. The engagement between foot-underlying portion 24 and foot engagement portion 14 may effectively couple elongated positioning member 16 to foot engagement portion 14. Additionally or alternatively, lower extremity orthosis 10 may be selectively adjustable in an overall length 48 via selective translation of lower leg-underlying portion 26 with respect to heel offloading device 30. For example, lower extremity orthosis 10 may be moved in the direction indicated by arrow 49, with respect to heel offloading device 30, to increase overall length 48, such as by detaching hook and loop fasteners 40, 42 from each other, and re-attaching lower leg-underlying portion 26 to a different location on outer surface 38 of heel offloading device 30 via hook and loop fasteners 40, 42 in a different position (e.g., along sleeve 44). As another example, lower extremity orthosis 10 may be moved in the direction indicated by arrow 49, with respect to heel offloading device 30, to increase overall length 48, by translating lower leg-underlying portion 26 within slot 46 of heel offloading device 30 to change the position of lower extremity orthosis 10 with respect to heel offloading device 30 (e.g., changing a distance between a distal end region 50 of heel offloading device 30 and sole-supporting surface 20 of foot engagement portion 14.

Foot engagement portion 14 of lower extremity orthosis 10 may include a cavity 52 configured to receive foot 12 without fully enclosing foot 12. In other words, while conventional boot devices at least substantially wholly envelop the patient's foot, often resulting in a hot, itchy, and/or otherwise uncomfortable device, cavity 52 of foot engagement portion 14 allows for airflow around foot 12 due to its open nature, which can significantly increase patient comfort and compliance with use of the device, while also allowing for inspection of the patient's foot by a clinician without having to remove lower extremity orthosis 10 from the patient's foot. In some examples, wound dressings may be accessible and changeable while the patient's foot is supported by lower extremity orthosis 10. In some examples, lower extremity orthosis 10 includes an elastic member 54 configured to secure foot 12 within cavity 52 of foot engagement portion 14, without completely surrounding or covering the patient's entire upper foot. Elastic member 54 may be formed of soft, breathable, thin, and/or elastic material, such that it functions to prevent foot 12 from accidentally falling out of foot engagement portion 14, without placing a significant or uncomfortable load on foot 12. Elastic member 54 may include one or more elastic straps, one or more elastic bands, and/or one or more elastic coverings that extend transversely and/or angularly across cavity 52 of foot engagement portion 14. Additionally or alternatively, the function of elastic member 54 may be provided by a strap, belt, covering, webbing, sheet, strip, or other fabric or textile that may not necessarily be elastic, but is generally flexible and comfortable to be secured against or across the top of the patient's foot.

Elastic member 54 may be fixedly and/or releasably secured to foot engagement portion 14. In a representative example, a first side of elastic member 54 may be fixedly secured to a first sidewall (e.g., one of opposing sidewalls 18) of foot engagement portion 14, while a second side of elastic member 54 may be releasably secured to a second sidewall (e.g., the other of opposing sidewalls 18) of foot engagement portion 14. In this manner, elastic member 54 may be partially released from foot engagement portion 14 such that it does not cross or obstruct cavity 52 while lower extremity orthosis 10 is being applied to foot 12, and then secured across the top of foot 12, such that elastic member 54 spans cavity 52, to prevent foot 12 from falling out of place from within cavity 52. The selectively releasable attachment of elastic member 54 may be formed via hook and loop fasteners, snaps, buttons, and/or any other suitable mechanism. In some examples, elastic member 54 may be releasably secured to both opposing sidewalls 18, while in other examples, elastic member 54 is releasably secured to just one opposing sidewall 18 of foot engagement portion 14. The tension of elastic member 54 may be selectively adjustable, such as by stretching elastic member 54 to a greater or lesser extent and/or applying an increased or decreased tension to elastic member 54 as it is applied across foot 12 and cavity 52 of foot engagement portion 14. Elastic member 54 may be relatively wider or narrower than represented in the figures, may be positioned closer to the patient's toes or ankle than represented in the figures, and/or may include two or more elastic members 54, which may be spaced apart and/or adjacent to one another.

In some examples of lower extremity orthosis 10, foot-underlying portion 24 of elongated positioning member 16 is at least partially inserted into foot engagement portion 14 of lower extremity orthosis 10. Additionally or alternatively, a lower surface 56 of lower leg-underlying portion 26 may be configured to engage with foot engagement portion 14, such as via a flap of foot engagement portion 14 that is secured to lower surface 56. Said lower surface 56 may correspond to a posterior side of lower extremity orthosis 10 when the device is worn, and/or may be an external surface of lower leg-underlying portion 26 that faces away from the patient's leg. Additionally or alternatively, an upper surface 58 of lower leg-underlying portion 26 may be configured to engage with heel offloading device 30. For example, hook and loop fasteners 40 may be positioned on upper surface 58 of lower leg-underlying portion 26 to secure lower extremity orthosis 10 to heel offloading device 30. Said upper surface 58 may correspond to an anterior side of lower extremity orthosis 10 when the device is worn, and/or may be an internal surface of lower leg-underlying portion 26 that faces the patient's leg. Additionally or alternatively, lower extremity orthosis 10 may be selectively and releasably coupled to heel offloading device 30 via one or more connecting or securement straps that may have hook and loop fasteners to engage with hook and loop fasteners 42 of heel offloading device 30. Said connecting straps may be secured to lower extremity orthosis 10 such as by being sewn or otherwise coupled to foot engagement portion 14 and/or lower leg-underlying portion 26, as will be described in further detail in connection with FIGS. 12 and 13.

Foot engagement portion 14 may be cushioned, such as by being formed of foam, fiberfill, air, gel, padding, memory foam, and/or other cushioning materials. Additionally or alternatively, foot engagement portion 14 may be formed of, or include, one or more bladders, which may be selectively or permanently filled, such as with air, water, gel, or other fluids. For example, foot engagement portion 14 may have one or more bladders that are configured to be selectively filled with water or air (or another substance) during use, and selectively emptied for storage and/or transport. In other examples, foot engagement portion 14 may have one or more bladders that are sealed, such that they are intended to remain filled. In some examples, the bladder or bladders may be filled to a greater or lesser extent, or the pressure may be increased or decreased within the bladder or bladders, so as to adjust the fit and/or firmness applied to the patient's foot via foot engagement portion 14.

In some examples, foot engagement portion 14 includes soft, flexible surfaces configured to cradle the patient's foot 12 without constricting it. Sole-supporting surface 20 of foot engagement portion 14 may be sized to be slightly or significantly wider than a typical human foot, to accommodate braces or wound dressings, and/or to allow for a variety of positions and adjustments of the position of foot 12 with respect to foot engagement portion 14, such that the patient may find a comfortable position without significant restriction. Additionally or alternatively, foot engagement portion 14 may be provided in a plurality of different sizes to better accommodate different sized feet comfortably. Sidewalls 18 of foot engagement portion 14 may be flexible with respect to sole-supporting surface 20, such that the angle of sidewalls 18 relative to sole-supporting surface 20 may be freely adjustable. In some examples, sidewalls 18 may splay downward when not restrained or held up by elastic member 54. In a specific example, sole-supporting surface 20 of foot engagement portion 14 is a cushioned foam support, with each of sidewalls 18 being cushioned foam supports as well, with a seam separating the cushioning materials of sole-supporting surface 20 and sidewalls 18 to provide some manner of selective articulation of sidewalls 18 with respect to sole-supporting surface 20, without creating a rigid, inflexible, or uncomfortable device for patients. Foot engagement portion 14 (e.g., sidewalls 18 and sole-supporting surface 20) may be configured to be pliable enough for patient comfort for the patient and yet still provide support for positioning of the patient's foot and snug conformity between foot engagement portion 14 and the patient's foot.

One or more elastic members 54 may be positioned and configured to support sidewalls 18 with respect to sole-supporting surface 20, thereby forming cavity 52 to receive foot 12 when elastic members 54 are secured across the device. One or both of sidewalls 18 may include hook and loop fasteners on an outer surface to receive one or more elastic members 54 to selectively secure them in place. Of course other types of fasteners or fastening devices are within the scope of the present disclosure for securing elastic members 54 with respect to foot engagement portion 14. Additionally or alternatively, foot engagement portion 14 may include a flexible, plastically deformable frame or internal structure that allows bending of sidewalls 18 and/or sole-supporting surface 20 to create the desired shape of cavity 52 to receive and comfortably cradle foot 12. Elastic member or members 54 may be positioned at various positions along the length of the patient's foot 12, such as near the patient's toes (e.g., the distal end of the patient's foot), near the middle of the foot, near the talus bone, and/or in other locations in between. Elastic members 54 also may be thinner in width, thicker in width, and/or different shapes than shown in the various examples illustrated and described herein.

Lower extremity orthosis 10 may be configured to be used by patients who are bedridden, on bedrest and/or in a supine or partially supine position for an extended period of time. That said, because lower extremity orthosis 10 may easily be selectively removed from heel offloading device 30, patients may ambulate easily if heel offloading device 30 is designed to allow patient ambulation. Lower extremity orthosis 10 is designed to maximize patient comfort, and allow as much movement as desired by the patient, which may increase patient compliance with use of lower extremity orthosis 10 and heel offloading device 30 as compared to prior art boot devices. Lower extremity orthosis 10 generally may be configured to support the patient's lower leg, heel, and foot without being too confining or restricting. Furthermore, the design of foot engagement portion 14 allows for inspection of the patient's foot 12 by healthcare personnel without removing the foot 12 from lower extremity orthosis 10. For example, foot engagement portion 14 may be configured to allow for checking pedal pulses, assessing capillary refill, and/or assessing foot temperature without removing lower extremity orthosis 10 from the patient's foot 12 (and/or by simply releasing elastic member 54 to allow such inspection, while the patient's foot 12 remains positioned between sidewalls 18 and against sole-supporting surface 20).

Lower extremity orthosis 10 may be selectively configurable for different sized patients, and/or may be configured to be customized for different sizes of patients. For example, lower extremity orthosis 10 may be provided in a plurality of sizes, which may be mixed and matched with a plurality of different sizes of heel offloading device 30 to create a customized support device for a given patient. Alternatively, a plurality of different sizes of lower extremity orthosis 10 may be combinable with a single size of heel offloading device 30. Additionally or alternatively, the size of cavity 52 created by foot engagement portion 14 may be selectively adjusted by positioning sidewalls 18 to allow for more space for a larger foot, or may be adjusted closer together to create a snugger fit for a smaller foot. Additionally or alternatively, heel offloading device 30 may be positioned at various locations along a length of elongated positioning member 16 of lower extremity orthosis 10, to accommodate longer or shorter legs by creating more or less space between heel offloading device 30 and foot engagement portion 14, based on the position of heel offloading device 30 along the length of elongated positioning member 16. In a specific example, elongated positioning member 16 may include one or more score lines or weakened areas along its length for selective adjustment of the length of elongated positioning member 16. For example, the length of elongated positioning member 16 may be selectively reduced by shortening elongated positioning member 16 at the score line (e.g., by removing a portion of elongated positioning member 16 by breaking it at a score line or weakened area).

FIG. 3 represents examples of heel offloading device 30 that may be used with presently disclosed lower extremity orthoses 10. With reference to FIGS. 1 and 3, heel offloading device 30 generally includes a concave member 62 that extends from a first end 64 to a second end 66. First end 64 is configured to engage the patient's lower leg 28 superior to the patient's ankle (i.e., the medial and lateral malleolus) 68, and is positioned within distal end region 50 of heel offloading device 30. Thus, heel offloading device 30 functions to offload and prevent formation of pressure ulcers on both the patient's heel 92 and ankle 68, even when the patient rotates their leg and/or is lying on their side. Second end 66 is configured to engage the patient's lower leg 28 distal to the patient's knee, such as at, or inferior to, the patient's mid-calf.

Heel offloading device 30 includes a first sidewall 70 and a second sidewall 72, each sidewall 70, 72 projecting from a floor 74 of concave member 62. An interior portion 76 of each of first and second sidewalls 70, 72, along with floor 74, together define a lower leg-receiving surface 78 that is configured to embrace the patient's lower leg 28 when heel offloading device 30 is worn by the patient. Heel offloading device 30 generally is configured such that the patient's heel 92, foot 12, and/or ankle 68 (see FIG. 1) are free from restraint by heel offloading device 30. In other words, heel offloading device 30 may be placed on the patient's lower leg 28 such that the patient's ankle 68 and heel 92 are distal to heel offloading device 30 and not contained between sidewalls 70, 72. Put yet another way, concave member 62 generally does not extend past the heel, ankle or foot when worn. Thus, heel offloading device 30 may be configured to be worn by patients during ambulation, and thus allow for patient mobility. Heel offloading device 30 also allows for inspection of the patient's heel when heel offloading device 30 is worn, without having to move or remove heel offloading device 30.

First and second sidewalls 70, 72 may be tapered to be thicker at first end 64 of concave member 62 (e.g., within distal end region 50 of heel offloading device 30) in at least one cross section, and thinner at second end 66 of concave member 62 in at least another cross section. In other words, sidewalls 70, 72 may be thinner where heel offloading device 30 engages the patient's lower leg 28 (thereby creating more space to receive and embrace the lower leg 28), and thicker where heel offloading device 30 engages the patient's lower leg farther down the leg, closer to the ankle, where the circumference of the lower leg is generally smaller than at the mid-calf area. The tapered nature of first and second sidewalls 70, 72 may be configured to impart functionality to heel offloading device 30 by keeping the patient's foot and ankle off of the surface on which the patient is resting (e.g., a bed, such as in the case of a patient on bedrest) when the patient rolls onto their side, rotates their legs, or otherwise adjusts their position on the surface. In other words, while heel offloading device 30 is configured to off-load the patient's heel and prevent heel ulcers, it also may be configured to prevent ankle ulcers that could occur if the patient rotated to their side on the bed and the ankle was allowed to be in contact with the bed surface for an extended period of time.

Having tapered first and second sidewalls 70, 72 may ensure that the patient's ankle does not contact the surface on which the patient is resting, thereby allowing the patient to rotate their legs while wearing the device so that they may rest in any comfortable position. Furthermore, tapered first and second sidewalls 70, 72 may be configured to avoid interference with the patient's ability to ambulate while wearing heel offloading device 30, whereas prior art devices often are not suitable to ambulate in, due to their bulky and non-tapered nature. Having tapered first and second sidewalls 70, 72 allows heel offloading device 30 to be thick enough in the relevant areas to prevent contact between the patient's ankle and the bed surface, and also thin enough in the relevant areas to not risk interference with mobility/ambulation. Prior art devices are generally not configured to stay on the patient's leg during an attempt to ambulate, and would be too wide and bulky to allow for ambulation, regardless. Furthermore, prior art devices generally do not provide room for the foot to be in any position other than upright, thereby preventing the patient from rotating or changing positions while using the device. Prior art boot-like devices present an increased fall risk if one attempts to ambulate while wearing them, and furthermore, do not protect the patient's ankle from bedsores if the patient were to lie on their side while wearing them because the ankle would contact the side of the boot in that position.

Additionally or alternatively, first and second sidewalls 70, 72 may vary in thickness with respect to one another. For example, first sidewall 70 may be thinner in one or more areas than corresponding areas of second sidewall 72, and/or first sidewall 70 may be thicker in one or more areas than corresponding areas of second sidewall 72. Concave member 62 may define a substantially U-shaped cross-section in at least one location along a length 84 of concave member 62. In some examples, substantially the entire length 84 of concave member 62 may be substantially U-shaped in cross-section, as represented in FIG. 3. Additionally or alternatively, concave member 62 may be a continuous, and/or monolithic, piece that extends between first and second opposing sidewalls 70, 72, and through floor 74 of concave member 62.

Floor 74 may be curved in some examples, and/or at least a portion of floor 74 may be substantially planar. In some examples, first and second sidewalls 70, 72 may be curved to meet floor 74 along interior portions 76. Additionally or alternatively, first and second sidewalls 70, 72 may be curved along an external surface 94 of sidewalls 70, 72, to meet a base 80. Base 80 generally underlies floor 74 when concave member 62 is in use, such that concave member 62 rests on a surface (e.g., a bed, chair, leg support, floor, etc.) with base 8 directly or indirectly contacting or engaging the surface. In some examples, at least a portion of base 80 is substantially flat. This can provide some level of stability for heel offloading device 30 on a given surface, such that it has a tendency to remain upright (e.g., resists unintentional rotation of heel offloading device 30 with respect to the resting surface), while still allowing ease of rotation when patients wish to adjust their position or leg orientation while wearing heel offloading device 30. In other words, heel offloading device 30 may be configured such that the patient can roll concave member 62 when turning the foot 12 or ankle 68, so as to reach a desired resting position. In some examples, base 80 may be rounded when unloaded.

The rounded sides of heel offloading device 30, combined with the fact that the patient's foot is unencumbered by the device, address patient concerns with prior art devices that were hot, bulky, uncomfortable, and/or impeded the ability to change positions or walk around. Because the patient's ankle is free from restraint by heel offloading device 30, patients can lie on their sides without heel offloading device 30 applying pressure to the patient's ankle. Similarly, lower extremity orthosis 10 may be designed such that foot engagement portion 14 does not apply pressure to the patient's heel or ankle when lying on their side. On the other hand, prior art boot-like devices would contact the patient's ankle if they turned the boot on its side, which could risk formation of pressure ulcers on the ankle and thus further discomfort and injury to the patient. Furthermore, lower extremity orthosis 10 may be designed to have as minimal bulk as possible while providing ample cushioning, and its open-air design allows for airflow to cool the patient's foot better than was possible with prior art devices. Furthermore, lower extremity orthosis 10 is selectively removable from heel offloading device 30 (e.g., by separating hook and loop fasteners 40, 42, thereby releasing lower extremity orthosis 10 from heel offloading device 30), thereby allowing for patient ambulation without removing heel offloading device from the patient's leg.

Additionally or alternatively, floor 74 of heel offloading device 30 may define a plurality of thicknesses in relation to a base 80 of heel offloading device 30. In other words, the thickness of floor 74 may vary along the length of heel offloading device 30. In a specific example, floor 74 may define at least three levels of thickness in relation to base 80, each of the three levels being different from any of the other three levels. In some examples, one of the at least three levels of different thicknesses may be present at first end 64, while a second of the at least three levels of different thicknesses may be present at second end 66 of concave member 62. In some examples, the thickness of floor 74 may be at a maximum about midway between first end 64 and second end 66. Generally, changes in thickness of floor 74 will form a continuous, smooth contour, which may be designed to optimize patient comfort and/or create a fit that corresponds to the shape and contours of the patient's lower leg.

Heel offloading device 30 may be formed of any suitable material, with patients' comfort and functionality of the device in mind. For example, heel offloading device 30 may be formed of a cell foam, a memory foam, and/or other pliable foam or cushioning material, which may be segmented, layered, and/or a continuous, monolithic piece. Additionally or alternatively, concave member 62 may be formed of, or include, one or more bladders, which may be selectively or permanently filled, such as with air, water, gel, or other fluids. For example, concave member 62 may have one or more bladders that are configured to be selectively filled with water or air (or another substance) during use, and selectively emptied for storage and/or transport. In other examples, concave member 62 may have one or more bladders that are sealed, such that they are intended to remain filled. In some examples, the bladder or bladders may be filled to a greater or lesser extent, or the pressure may be increased or decreased within the bladder or bladders, so as to adjust the fit and/or firmness applied to the patient's lower leg via concave member 62. Concave member 62 (e.g., first and second sidewalls 70, 72) is generally substantially pliable, which can allow for both comfort for the patient and snug conformity between concave member 62 and the patient's lower leg 28. The material selected for concave member 62 may be configured to minimize the depth and bulk of the foam or other material, such that heel offloading device 30 may be configured to elevate the patient's heel 92 off of a resting surface while minimizing any impediment to ambulation and mobility of the patient's leg. Additionally, such a design allows for inspection of the patient's heel 92 without removing the lower leg 28 from the heel offloading device 30 because the patient's heel and ankle are free from restraint by heel offloading device 30 (in other words, the patient's heel and ankle are not constrained by, or positioned within, heel offloading device 30).

In some examples, heel offloading device 30 includes a form-fitting shell 82 that at least partially encloses concave member 62 of heel offloading device 30. For example, form-fitting shell 82 may include an opening through which it may receive concave member 62 within form-fitting shell 82, such that all or some of concave member 62 is selectively removably contained within form-fitting shell 82. In other words, concave member 62 may be inserted through an opening into form-fitting shell 82. Form-fitting shell 82 generally is constructed of a flexible and/or elastic fabric material that conforms to concave member 62. In specific examples, form-fitting shell 82 may be formed of 4-way stretch material. Additionally or alternatively, form-fitting shell 82 may be waterproof, water repellant, and/or water resistant, and thus may be configured to protect concave member 62 when concave member 62 is contained within form-fitting shell 82. Form-fitting shell 82 may be secured around concave member 62, such as via one or more zippers, via hook-and-loop fasteners, and/or via one or more other releasable fasteners or closures. Form-fitting shell 82 may be selectively removable from concave member 62 for washing or sterilization, or replacement with a new or different form-fitting shell 82. Form-fitting shell 82 may be configured to envelop first and second opposing sidewalls 70, 72 and base 80 of concave member 62, such that interior portions 76 of sidewalls 70, 72 and floor 74 are free from seams or coupling devices. Heel offloading device 30 may include a releasable material 86 (e.g., one side of a hook and loop fastener) extending along at least a portion of a length 84 of concave member 62, and/or along at least a portion of form-fitting shell 82. In some examples, one or more areas of releasable material 86 may be present on form-fitting shell 82, and/or directly on concave member 62, such as for securing a cover 90 and/or a stabilizing structure 88.

With reference to FIG. 1, systems 5 may include a stabilizing structure 88 that is configured to stabilize heel offloading device 30, such as to prevent rotation of heel offloading device 30 relative to the surface on which the patient is resting. In some examples, stabilizing structure 88 may be selectively releasably coupled to heel offloading device 30, such as via being coupled to releasable material 86 (e.g., hook and loop fasteners) on concave member 62 and/or releasable material 86 on form-fitting shell 82 surrounding concave member 62. In some examples, stabilizing structure 88 may simply be placed adjacent, and/or wedged against, first sidewall 70 and/or second sidewall 72 to stabilize concave member 62. In some examples, stabilizing structure 88 tends to stay in place in relation to heel offloading device 30 simply due to friction between the materials used to form stabilizing structure 88 and form-fitting shell 82, rather than being proactively fastened or secured via hook and loop fasteners or other fasteners. Stabilizing structure 88 may be, for example, a wedge, a block, or a triangular structure, such that stabilizing structure 88 may be configured to resist rotation of itself, and also engage with heel offloading device 30 to stabilize the position and orientation of heel offloading device 30.

Heel offloading device 30 may include a cover 90 that may extend between portions of form-fitting shell 82, along at least a portion of length 84 of concave member 62, and/or transversely across floor 74 of heel offloading device 30, between first sidewall 70 and second sidewall 72. For example, cover 90 may be coupled to first sidewall 70 or second sidewall 72 (e.g., sewn to form-fitting shell 82 in the area covering one of sidewalls 70, 72), and selectively releasably securable to the other of first sidewall 70 and second sidewall 72. In this manner, cover 90 may be configured to be selectively uncoupled from form-fitting shell 82 (or selectively uncoupled from first sidewall 70 and/or second sidewall 72). Said uncoupling of one or both sides of cover 90 may allow for the patient's leg 28 to be inserted into concave member 62 (e.g., embraced by sidewalls 70, 72 and placed against lower leg-receiving surface 78 of heel offloading device 30). Cover 90 may be secured on both sides while it is desired to retain the patient's leg 28 within heel offloading device 30, and the again uncoupled along one or both sides to remove heel offloading device 30 from the patient's leg 28.

In a specific example, one side of cover 90 may be sewn or otherwise coupled to first sidewall 70, and may be stretched transversely across floor 74 such that the opposite side of cover 90 may be releasably secured to second sidewall 72, such as via hook and loop fasteners. When secured (e.g., when cover 90 is selectively coupled to form-fitting shell 82 or to first sidewall 70 and/or second sidewall 72), cover 90 may be configured to bias first and second sidewalls 70, 72 towards one another against the patient's lower leg 28. In some examples, cover 90 may be integral with form-fitting shell 82, or may be coupled to form-fitting shell 82. In other words, form-fitting shell 82 may include cover 90, in some examples. Additionally or alternatively, cover 90 may be directly coupled to concave member 62. Cover 90 may be configured to cover and/or extend across at least a portion of the patient's shin (e.g., the anterior side of the patient's lower leg 28) when heel offloading device 30 is worn by the patient. Cover 90 may be a flexible, soft fabric material, such as nylon, or other suitable materials. The function of cover 90 may be provided by a strap, belt, covering, webbing, sheet, strip, and/or other fabric or textile that may not necessarily be elastic, but is generally flexible and comfortable to be secured against or across the top of the patient's lower leg. Cover 90 is configured to prevent accidental or unintentional removal of heel offloading device 30 from the patient's lower leg 28. In other words, because cover 90 may be stretched across the top of the patient's lower leg 28 and connected to both sides of heel offloading device 30, cover 90 may function to prevent the leg from lifting out away from lower leg-receiving surface 78, thereby retaining heel offloading device 30 in position on the patient's lower leg 28 such that heel offloading device 30 continues to embrace the patient's lower leg 28 even if the patient lifts their leg off the resting surface. One or both sides of cover 90 may be released to facilitate removal of heel offloading device 30 from the patient's lower leg 28.

Turning now to FIGS. 4-10 and 12-13, illustrative non-exclusive examples of systems 5 including lower extremity orthoses 10 are illustrated. Where appropriate, the reference numerals from the schematic illustrations of FIGS. 1-3 are used to designate corresponding parts in FIGS. 4-10 and 12-13; however, the examples of FIGS. 4-10 and 12-13 are non-exclusive and do not limit systems 5 or lower extremity orthoses 10 to the illustrated examples of FIGS. 4-10 and 12-13. That is, systems 5 and lower extremity orthoses 10 are not limited to the specific examples illustrated in FIGS. 4-10 and 12-13 and may incorporate any number of the various aspects, configurations, characteristics, properties, etc. that are illustrated in and discussed with reference to the schematic representations of FIGS. 1-3 and/or the examples of FIGS. 4-10 and 12-13, as well as variations thereof, without requiring the inclusion of all such aspects, configurations, characteristics, properties, etc. For the purpose of brevity, each previously discussed component, part, portion, aspect, region, etc. or variants thereof may not be discussed, illustrated, and/or labeled again with respect to each of FIGS. 4-10 and 12-13; however, it is within the scope of the present disclosure that the previously discussed features, variants, etc. may be utilized with the same.

Figure 4:
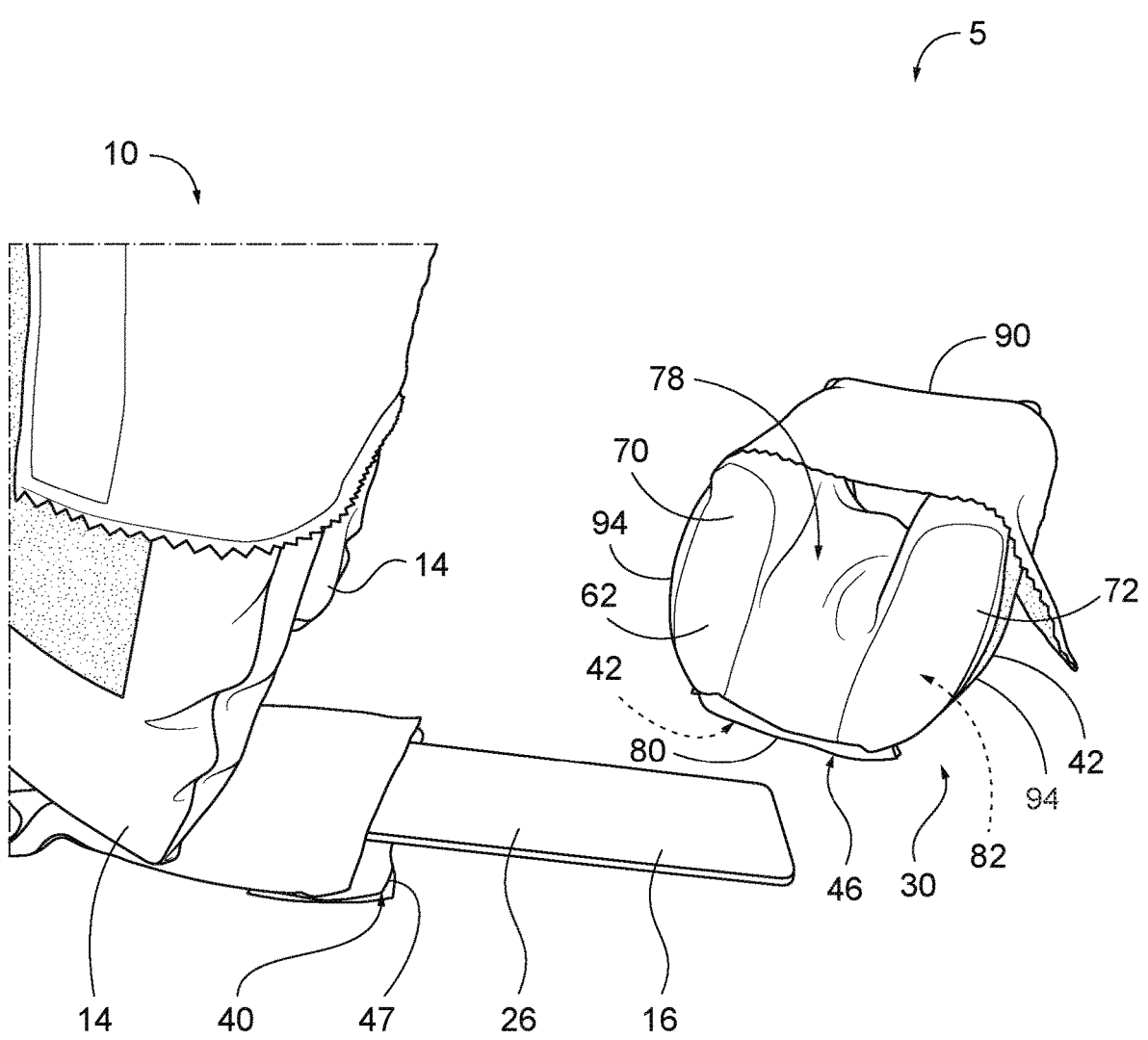
FIG. 4 is a perspective view of an example of a system according to the present disclosure, showing an example of a lower extremity orthosis separated from an example of a heel offloading device.

FIG. 4 shows an example of system 5 with heel offloading device 30 and lower extremity orthosis 10, which are shown separated, for clarity. In this example, a portion of lower leg-underlying portion 26 of elongated positioning member 16 of lower extremity orthosis 10 is shown extending outwardly. Elongated positioning member 16 continues into foot engagement portion 14 of lower extremity orthosis 10. In this example, heel offloading device 30 includes a slot or pocket 46 into which the exposed portion of elongated positioning member 16 may be inserted, to couple lower extremity orthosis 10 to heel offloading device 30. The extent to which elongated positioning member 16 is inserted into slot or pocket 46 can determine the overall length of the system 5. For example, elongated positioning member 16 may be inserted into pocket 46 to a greater extent to bring lower extremity orthosis 10 and heel offloading device 30 closer together (thereby shortening the overall length of the combined devices), or elongated positioning member 16 may be inserted into pocket 46 to a lesser extent to increase the distance between lower extremity orthosis 10 and heel offloading device 30, thereby increasing the overall length of the combined devices (or elongated positioning member 16 may be partially pulled out from pocket 46 to accomplish the same).

Pocket 46 may be formed in form-fitting shell 82 covering concave member 62, as shown in FIG. 4, and may be positioned adjacent base 80 of heel offloading device 30. In other examples, heel offloading device 30 may include one or more pockets 46 in additional and/or different locations to receive one or more elongated positioning members 16 from lower extremity orthosis 10. For example, form-fitting shell 82 may include one or more additional or alternatively-placed pockets 46, or one or more pockets 46 may be formed directly in concave member 62. Pocket 46 generally extends longitudinally along length 84 of concave member 62, and generally has a width sufficient to receive elongated positioning member 16 with a snug fit, such that elongated positioning member 16 may be easily inserted into pocket 46, though without excessive extra room for lateral movement of elongated positioning member 16 within pocket 46, to facilitate a stable and secure coupling between heel offloading device 30 and lower extremity orthosis 10. To selectively secure the positioning of heel offloading device 30 relative to lower extremity orthosis 10 once elongated positioning member 16 is inserted to the desired extent into pocket 46, a flap 47 on lower extremity orthosis 10 containing hook and loop fasteners 40 may be releasably secured to hook and loop fasteners 42 on heel offloading device 30. For example, form-fitting shell 82 on heel offloading device 30 may include one or more areas of hook and loop fasteners 42, such as on external surfaces 94 of one or both sidewalls 70, 72, and/or on base 80. In the example of FIG. 4, heel offloading device 30 includes hook and loop fasteners 42 on base 80 to engage with hook and loop fasteners 40 of lower extremity orthosis 10 (e.g., on flap 47), and heel offloading device 30 also includes hook and loop fasteners 42 on external surface 94 of sidewall 72 to engage with cover 90 of heel offloading device 30. In various examples of lower extremity orthosis 10, flap 47 may be longer and/or include a larger area of hook and loop fasteners 40, and thereby may be configured for custom fitting based on the patient's height and/or leg length.

Figure 5:
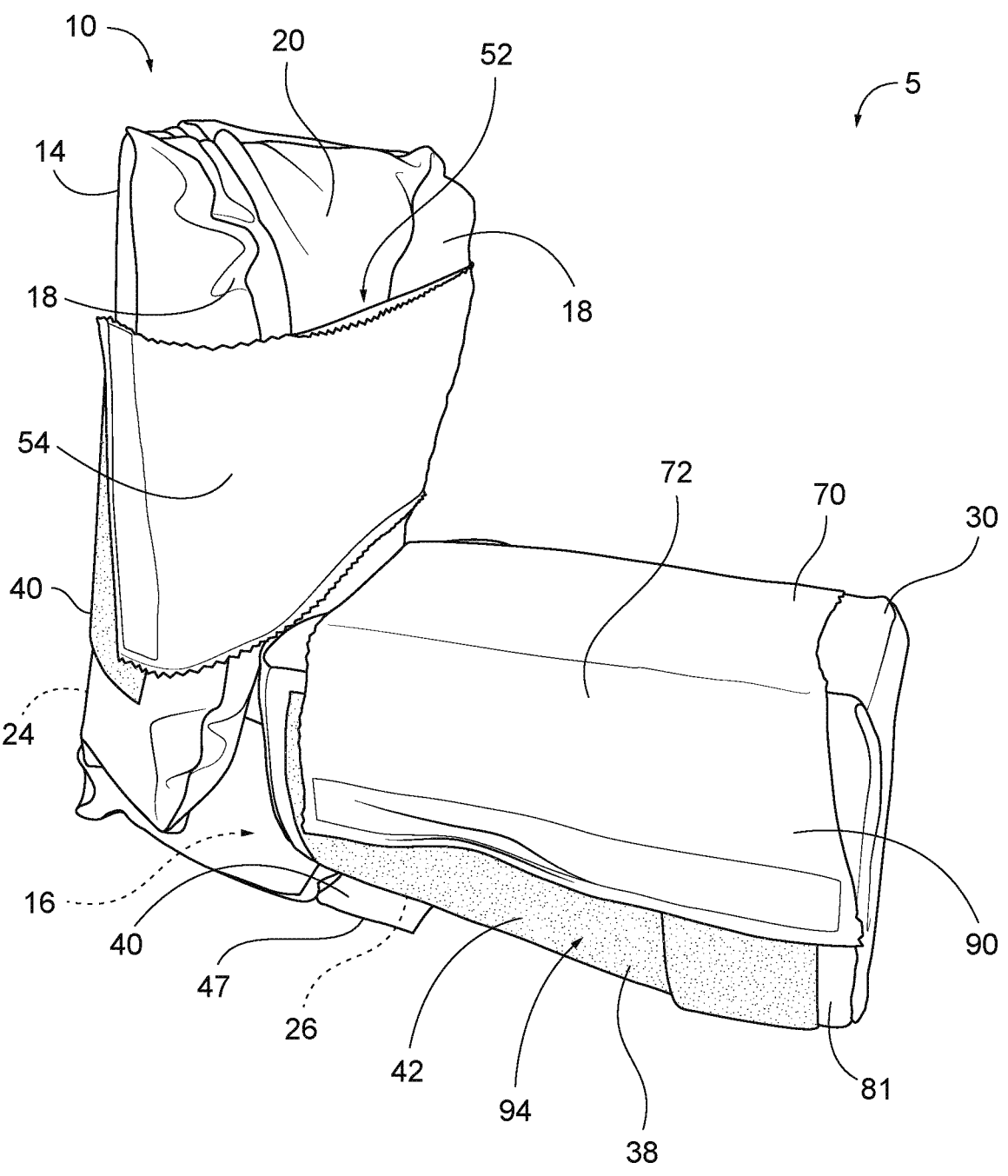
FIG. 5 is a perspective view of an example of a system according to the present disclosure, showing an example of a lower extremity orthosis releasably coupled to an example of a heel offloading device.

FIG. 5 illustrates system 5 of FIG. 4, with lower extremity orthosis 10 coupled to heel offloading device 30 via insertion of elongated positioning member 16 into pocket 46 of heel offloading device 30. Thus, foot-underlying portion 24 of elongated positioning member 16 serves to couple elongated positioning member 16 to foot engagement portion 14 such that lower extremity orthosis 10 may be selectively and removably engaged with heel offloading device 30 via lower leg-underlying portion 26 of elongated positioning member 16. Flap 47 of lower extremity orthosis 10 with hook and loop fasteners 40 that may be secured to hook and loop fasteners 42 on base 80 of heel offloading device 30 is visible in FIG. 5. FIG. 5 also illustrates an example of hook and loop fasteners 42 on external surface 94 of sidewall 72 to secure cover 90 in place once it is stretched transversely across the top of heel offloading device 30. Cover 90 may be releasably secured to the opposite sidewall (e.g., sidewall 70) via corresponding hook and loop fasteners 42 on sidewall 70, or cover 90 may be affixed to sidewall 70 such as via stitching or sewing cover 90 along that side of heel offloading device 30.

FIG. 5 also illustrates an example of elastic member 54 that is stretched across cavity 52 between sidewalls 18 of foot engagement portion 14 of lower extremity orthosis 10. Similar to cover 90, one or both sides of elastic member 54 may be releasably secured to foot engagement portion 14 via hook and loop fasteners 40 on one or both sidewalls 18 and/or one side of elastic member 54 may be sewn or stitched to be affixed to one of sidewalls 18. In this manner, elastic member 54 may be comfortably stretched across the top of the patient's foot once the foot is positioned within cavity 52 of foot engagement portion 14, and cover 90 may be comfortably stretched across the top of the patient's lower leg once the lower leg is positioned within heel offloading device 30. Elastic member 54 may be configured to bias sidewalls 18 towards each other to cradle or snug up to the patient's foot. When lower extremity orthosis 10 is secured to heel offloading device 30 it may engage with the patient's foot to prevent or reduce plantar flexion while wearing heel offloading device 30.

In the example of FIG. 5, form-fitting shell 82 includes an envelope closure flap 81 to assist with releasably closing or placing form-fitting shell 82 around concave member 62 to enclose concave member 62 therein. To remove concave member 62 from form-fitting shell 82, envelope closure flap 81 may be flipped up to expose the opening of form-fitting shell 82, through which concave member 62 may be removed. In other words, envelope closure flap 81 may obscure a hole or opening of form-fitting shell 82 through which concave member 62 can be selectively removably inserted into form-fitting shell 82. Additionally or alternatively, form-fitting shell 82 may include one or more zippers or other closures to assist with removal and donning of form-fitting shell 82 with respect to concave member 62. In some examples, hook and loop fasteners 42 also may be present or included on envelope closure flap 81. As noted herein, form-fitting shell 82 may be configured for easy removal from concave member 62 (e.g., without damaging form-fitting shell 82 or concave member 62), such as to wash and/or sterilize form-fitting shell 82.

Figure 6:
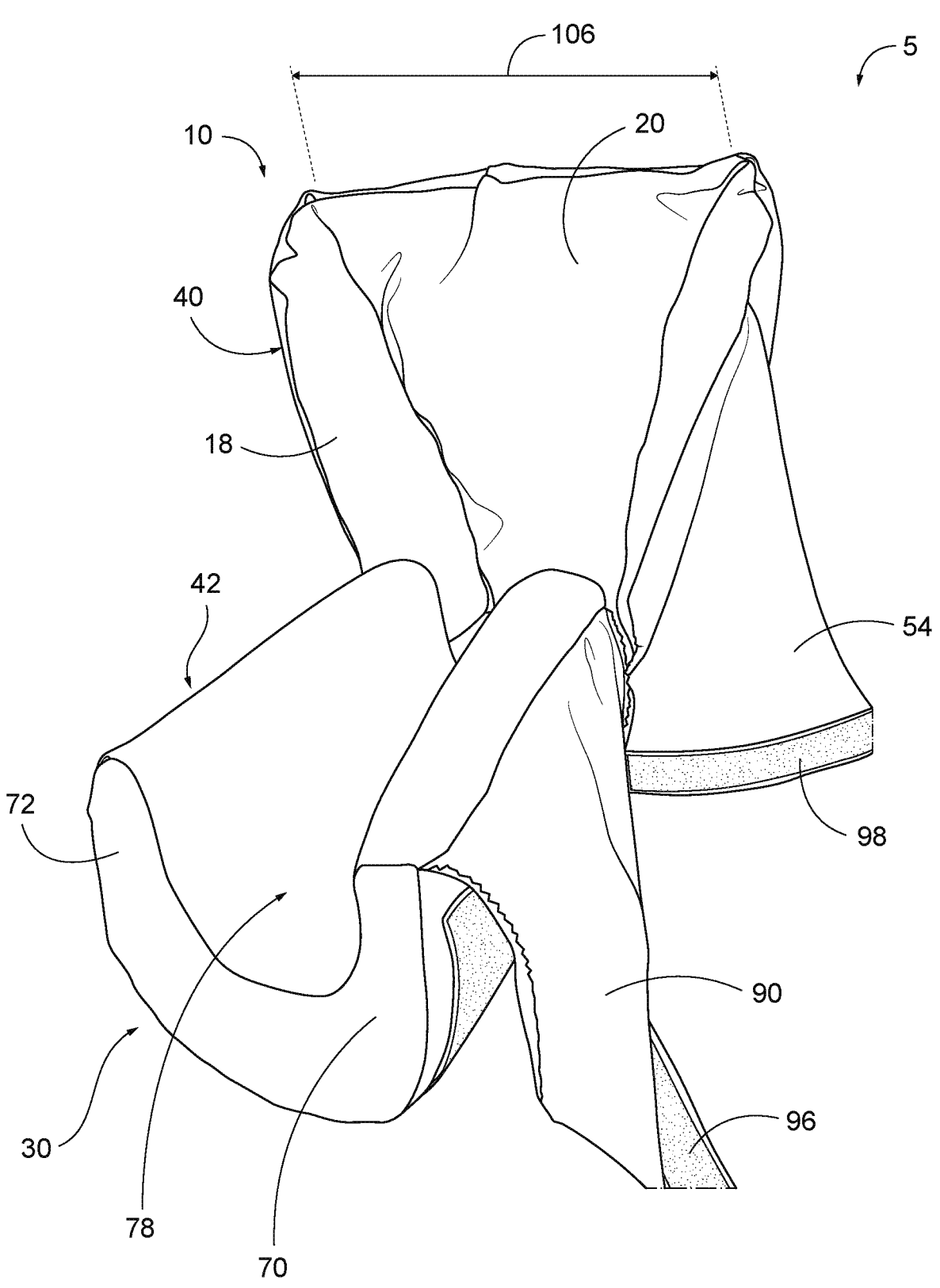
FIG. 6 is a perspective view of an example of a system according to the present disclosure, showing an example of a lower extremity orthosis releasably coupled to an example of a heel offloading device, with a cover of the heel offloading device open, and an elastic member of the lower extremity orthosis open.

FIG. 6 shows a front perspective view of an example of system 5, with lower extremity orthosis 10 being coupled to heel offloading device 30, and with both cover 90 being unsecured from one sidewall of heel offloading device 30, and elastic member 54 being unsecured from one sidewall 18 of foot engagement portion 14. In this configuration, the patient's lower leg may be placed between sidewalls 70, 72 of heel offloading device 30, and against lower leg-receiving surface 78, and the patient's foot may be placed between sidewalls 18 of foot engagement portion 14, such that the sole of the patient's foot is placed against, facing, and/or adjacent sole-supporting surface 20. Cover 90 may be stretched across the top of the patient's lower leg, and hook and loop fasteners 96 on cover 90 may be secured to hook and loop fasteners 42 on sidewall 72 to help retain the patient's lower leg within heel offloading device 30. Similarly, elastic member 54 may be stretched across the top of the patient's foot, and hook and loop fasteners 98 on elastic member 54 may be secured to hook and loop fasteners 40 on foot engagement portion 14 to help retain the patient's foot within lower extremity orthosis 10. Cover 90 and elastic member 54 may be thin, breathable, elastic fabrics with a soft texture that are comfortable to the patient. Similarly, fabrics used for form-fitting shell 82 along lower leg-receiving surface 78 of heel offloading device 30, cushioning materials used for concave member 62, fabrics used to cover sole-supporting surface 20 of lower extremity orthosis 10, and cushioning materials used for sole-supporting surface 20 and sidewalls 18 all may be selected to maximize patient comfort, and thereby may increase patient compliance with use of system 5.

Figure 7:
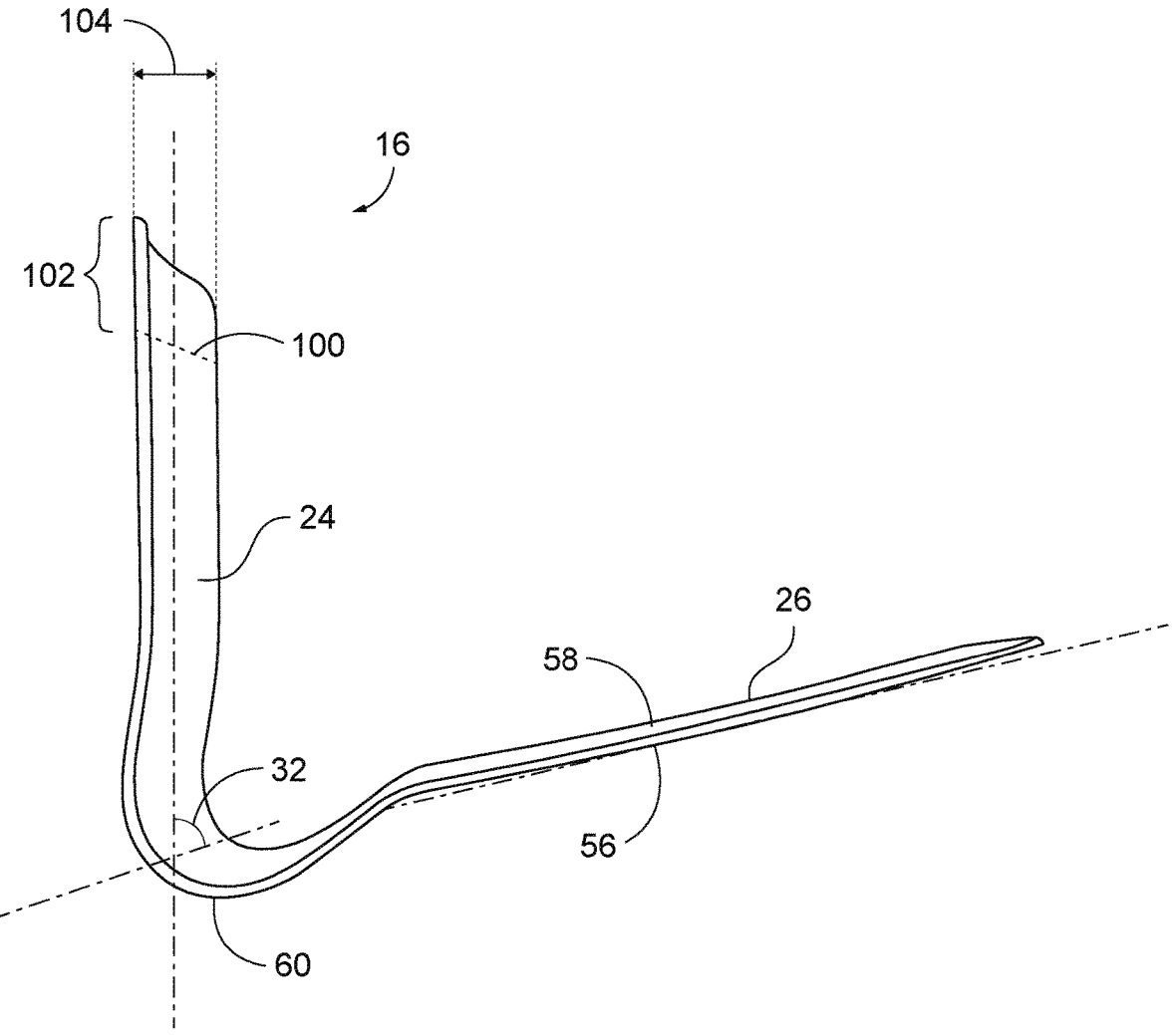
FIG. 7 illustrates a perspective view of an example of an elongated positioning member that may be a component of presently disclosed lower extremity orthoses.

FIG. 7 illustrates elongated positioning member 16 removed from lower extremity orthosis 10 and heel offloading device 30, to more clearly illustrate foot-underlying portion 24, curved heel portion 60, and lower leg-underlying portion 26. Foot-underlying portion 24 is contained within or secured to foot engagement portion 14 of lower extremity orthosis 10, and lower leg-underlying portion 26 is secured to heel offloading device 30. For example, foot-underlying portion 24 may be inserted into foot engagement portion 14 such that it is inferior to sole-supporting surface 20 of foot engagement portion 14. In this manner, the cushioning materials of sole-supporting surface 20 separate the patient's foot from foot-underlying portion 24 of elongated positioning member 16. In this manner, elongated positioning member 16 may provide a frame or structure to foot engagement portion 14 without contacting the patient's foot, and therefore without introducing discomfort to the patient. In some examples, a width 104 of foot-underlying portion 24 may be less than a width 106 of foot engagement portion 14 (FIG. 6), though in other examples, width 104 of foot-underlying portion 24 may substantially correspond to width 106 of foot engagement portion 14.

As shown in FIG. 7, elongated positioning member 16 may be a single, integrally formed monolithic body. In some examples, elongated positioning member 16 may be a relatively thin sheet of plastic, carbon fiber reinforced polymer, metal, and/or other material. Elongated positioning member 16 generally is at least semi-rigid to maintain its shape and provide support and positioning for lower extremity orthosis 10 relative to heel offloading device 30. In some examples, elongated positioning member 16 may be slightly elastically or plastically deformable to allow for adjustments of system 5. For example, the angle 32 between foot-underlying portion 24 and lower leg-underlying portion 26 may be adjusted slightly by bending foot-underlying portion 24 relative to lower leg-underlying portion 26. Additionally or alternatively, elongated positioning member 16 may be hinged to allow such adjustment of angle 32. Angle 32 is generally slightly acute, though may be close to 90 degrees, 90 degrees, or even greater than 90 degrees in some examples.

Additionally or alternatively, foot-underlying portion 24 and/or lower leg-underlying portion 26 may include one or more score lines or weakened areas to facilitate selective reduction of the length of foot-underlying portion 24 and/or lower leg-underlying portion 26. For example, FIG. 7 illustrates a score line 100 across foot-underlying portion 24, which may be a thinned or weakened area of foot-underlying portion 24 to facilitate removal of portion 102 of foot-underlying portion 24 to shorten its length. Of course, foot-underlying portion 24 and/or lower leg-underlying portion 26 may include one or more score lines in various locations, if desired. For example, foot-underlying portion 24 may include one or more score lines 100, and/or lower leg-underlying portion 26 may include one or more score lines 100. Score line or lines 100 may be configured to allow for quick and easy customization in the form of changes to the length of foot-underlying portion 24 and/or lower leg-underlying portion 26, such as by allowing a portion of elongated positioning member 16 to be snapped off, or easily cut or otherwise removed. This may enable elongated positioning member 16 to be somewhat customized to fit different sizes of patients by a clinician familiar with caring for patients in need of disclosed systems 5. For example, by adjusting the length of foot-underlying portion 24 by removing a portion of foot-underlying portion 24 above a respective score line 100, one in turn adjusts the distance of lower extremity orthosis 10 from heel offloading device 30 once lower extremity orthosis 10 is secured to heel offloading device 30 via elongated positioning member 16. In examples where foot-underlying portion 24 and/or lower leg-underlying portion 26 have two or more score lines 100, said score lines 100 may be equally spaced apart, may be adjacent the respective ends of elongated positioning member 16, and/or may include relevant markings or indicia, such as related to respective sizes or measurements for the respective score lines 100.

Curved heel portion 60 is generally sized and shaped to ensure that the patient's heel is not contacted by elongated positioning member 16 or any other portion of lower extremity orthosis 10 when the device is worn by a patient. FIG. 7 is not drawn to scale, and elongated positioning member 16 is not limited to the relative dimensions and shapes illustrated in the example of FIG. 7. For example, lower leg-underlying portion 26 may be shorter relative to foot-underlying portion 24 than is shown in the example of FIG. 7, and/or foot-underlying portion 24 may be longer relative to lower leg-underlying portion 26 than shown in the example of FIG. 7. Additionally or alternatively, elongated positioning member 16 may be relatively wider or narrower in various locations than is shown in various FIGS. herein. In addition to or instead of having one or more score lines 100 for adjustment of the size of elongated positioning member 16, elongated positioning member 16 may be provided in two or more sizes to accommodate various sized patients. For example, elongated positioning members 16 may be provided in adult and pediatric sizes. Additionally or alternatively, elongated positioning members 16 may be provided in various sizes based on dimensions or measurements, and/or in traditional sizing options such as small, medium, and large.

Figure 8:
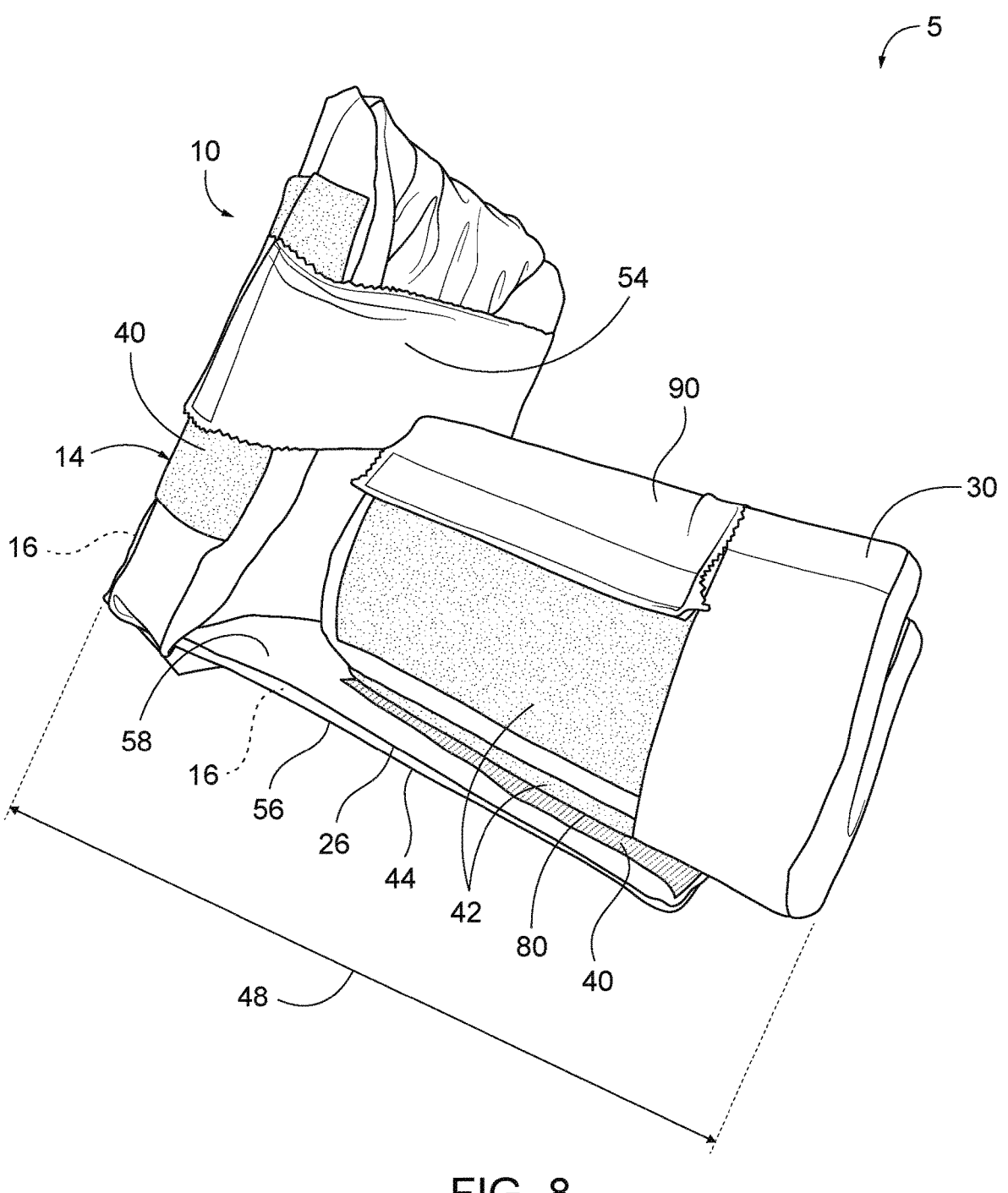
FIG. 8 is a perspective view of an example of a system according to the present disclosure, showing an example of a lower extremity orthosis releasably coupled to an example of a heel offloading device.

FIG. 8 illustrates another example of system 5 with heel offloading device 30 shown releasably secured to lower extremity orthosis 10. Elongated positioning member 16 is not directly visible in FIG. 8, as foot-underlying portion 24 is engaged with and contained within foot engagement portion 14, and lower leg-underlying portion 26 is contained within sleeve 44. In the example of FIG. 8, heel offloading device 30 is secured to lower extremity orthosis 10 via engagement between hook and loop fasteners 42 on heel offloading device 30 (e.g., an area of hook and loop fasteners 42 on base 80 of heel offloading device 30) and corresponding hook and loop fasteners 40 on lower extremity orthosis 10 (e.g., hook and loop fasteners 40 on upper surface 58 of sleeve 44 on lower leg-underlying portion 26 of elongated positioning member 16). Thus, foot-underlying portion 24 of elongated positioning member 16 serves to couple elongated positioning member 16 to foot engagement portion 14, such that lower extremity orthosis 10 may be selectively and removably engaged with heel offloading device 30 via lower leg-underlying portion 26 of elongated positioning member 16. Lower extremity orthosis 10 also includes hook and loop fasteners 40 on foot engagement portion 14 for securing elastic member 54, and heel offloading device 30 also includes hook and loop fasteners 42 on external surface 94 of one or both sidewalls 70, 72 to secure cover 90, in this example.

Figure 9:
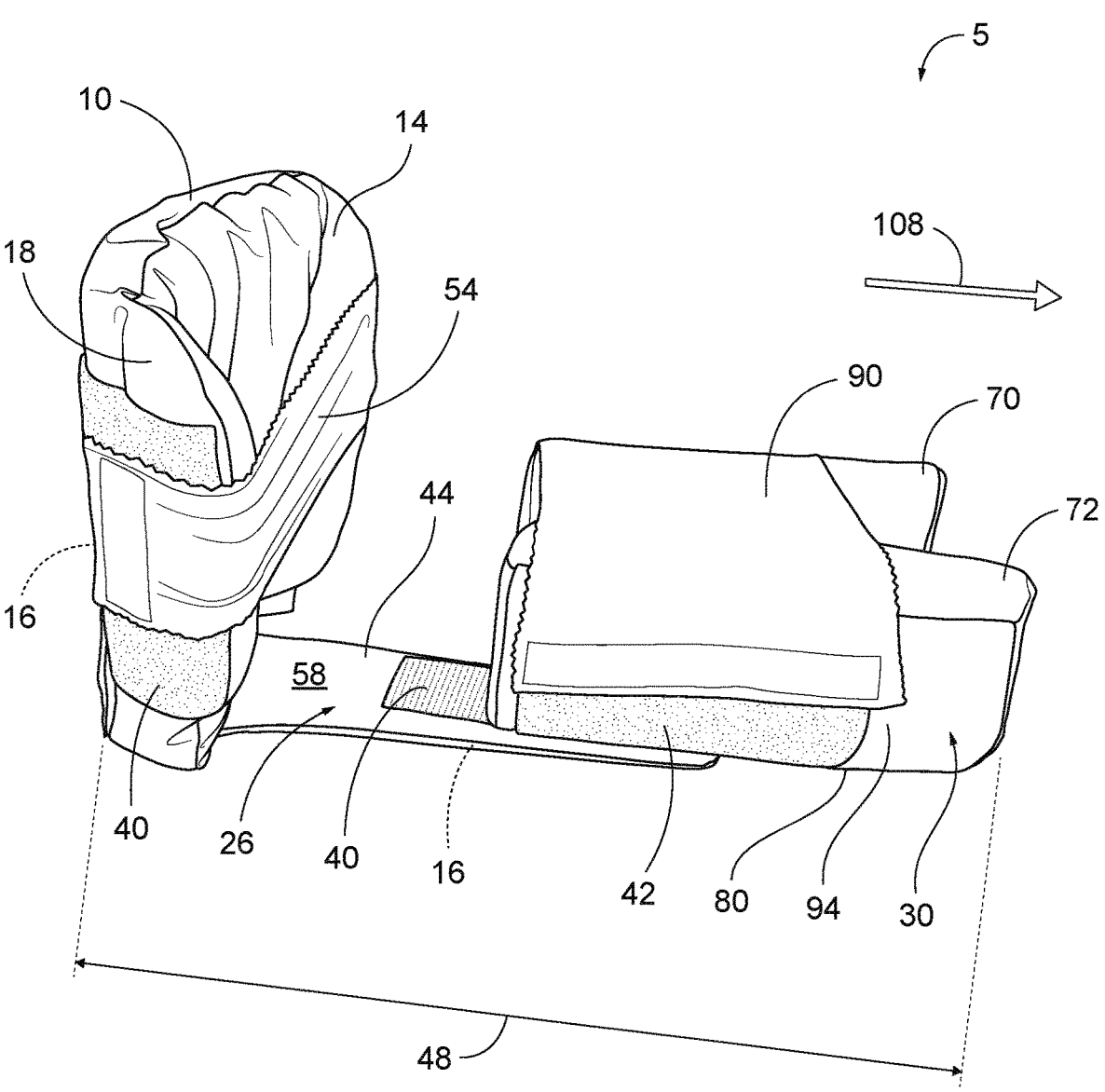
FIG. 9 is a side view of the system of FIG. 8, with the heel offloading device positioned relative to the lower extremity orthosis to extend the overall length of the system, as compared to the respective positions and length of the system illustrated in FIG. 8.

Overall length 48 of system 5 may be adjusted by translating heel offloading device 30 with respect to lower extremity orthosis 10. For example, as shown in FIG. 9, heel offloading device 30 may be translated away from foot engagement portion 14 along lower leg-underlying portion 26 (e.g., in the direction indicated by arrow 108) to increase the distance between foot engagement portion 14 and heel offloading device 30, thereby increasing overall length 48 in FIG. 9 as compared to overall length 48 in FIG. 8. To move heel offloading device 30, respective hook and loop fasteners 40, 42 may be separated from each other to release heel offloading device 30 from hook and loop fasteners 40 on sleeve 44. Then, heel offloading device 30 may be reattached to hook and loop fasteners 40 on sleeve 44 in a different position to increase or decrease overall length 48 as desired.

Figure 10:
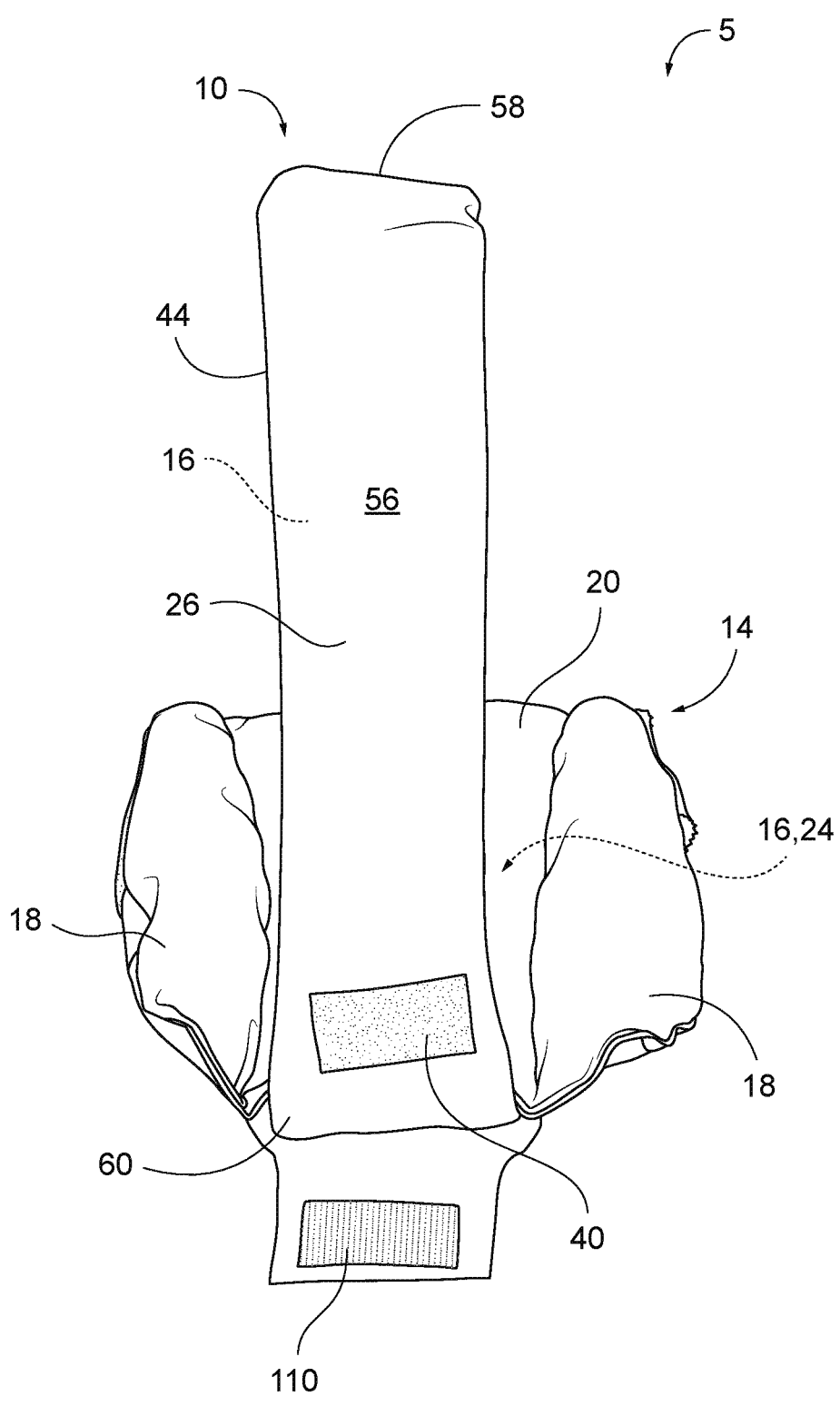
FIG. 10 is a bottom view of an example of a lower extremity orthosis according to the present disclosure.

FIG. 10 illustrates an example of lower extremity orthosis 10, shown without heel offloading device 30. In FIG. 10, lower extremity orthosis 10 is shown tilted upwards to illustrate lower surface 56 of lower leg-underlying portion 26 of elongated positioning member 16 (which is inside sleeve 44 in this example). Elongated positioning member 16 continues through curved heel portion 60 and foot-underlying portion 24, which is obscured by foot engagement portion 14. Sleeve 44 may include hook and loop fasteners 40 on upper surface 58 to engage with heel offloading device 30, and as FIG. 10 illustrates, sleeve 44 additionally or alternatively may include hook and loop fasteners 40 on lower surface 56, which may be configured to be secured to corresponding hook and loop fasteners 110 on foot engagement portion 14 to secure sleeve 44 in place on elongated positioning member 16. This configuration may allow removal of elongated positioning member 16 entirely from foot engagement portion 14. In other examples, however, sleeve 44 may be omitted, or sleeve 44 may be affixed to foot engagement portion 14 via stitching or sewing, or another fastening mechanism. While hook and loop fasteners 40 are described herein as being included on sleeve 44, in some examples said hook and loop fasteners 40 may be present directly on elongated positioning member 16 (e.g., embedded in elongated positioning member 16 and/or adhered to elongated positioning member 16).

Figure 12:
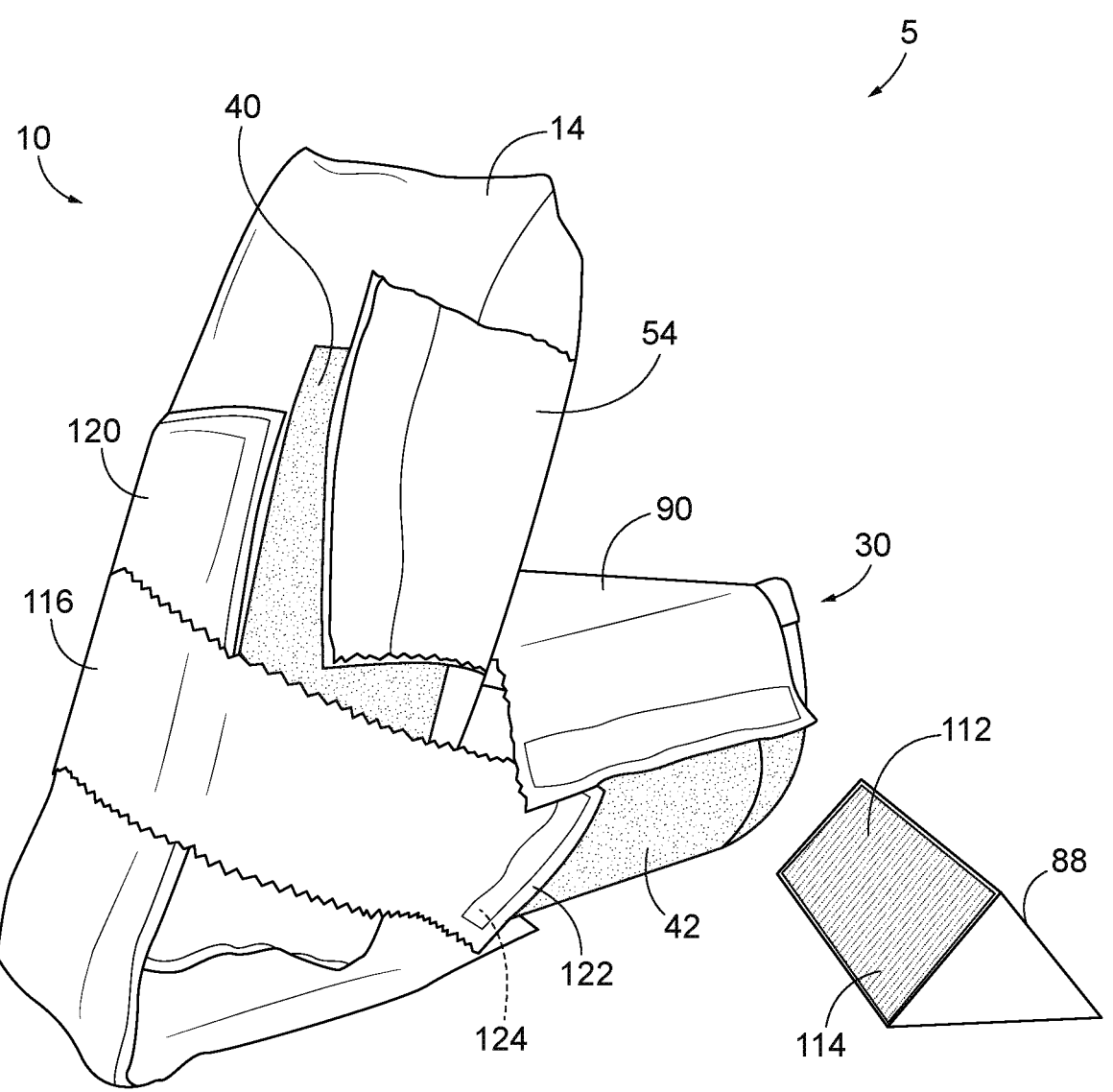
FIG. 12 is a bottom perspective view of an example of a heel offloading device selectively releasably secured to a lower extremity orthosis.
Figure 13:
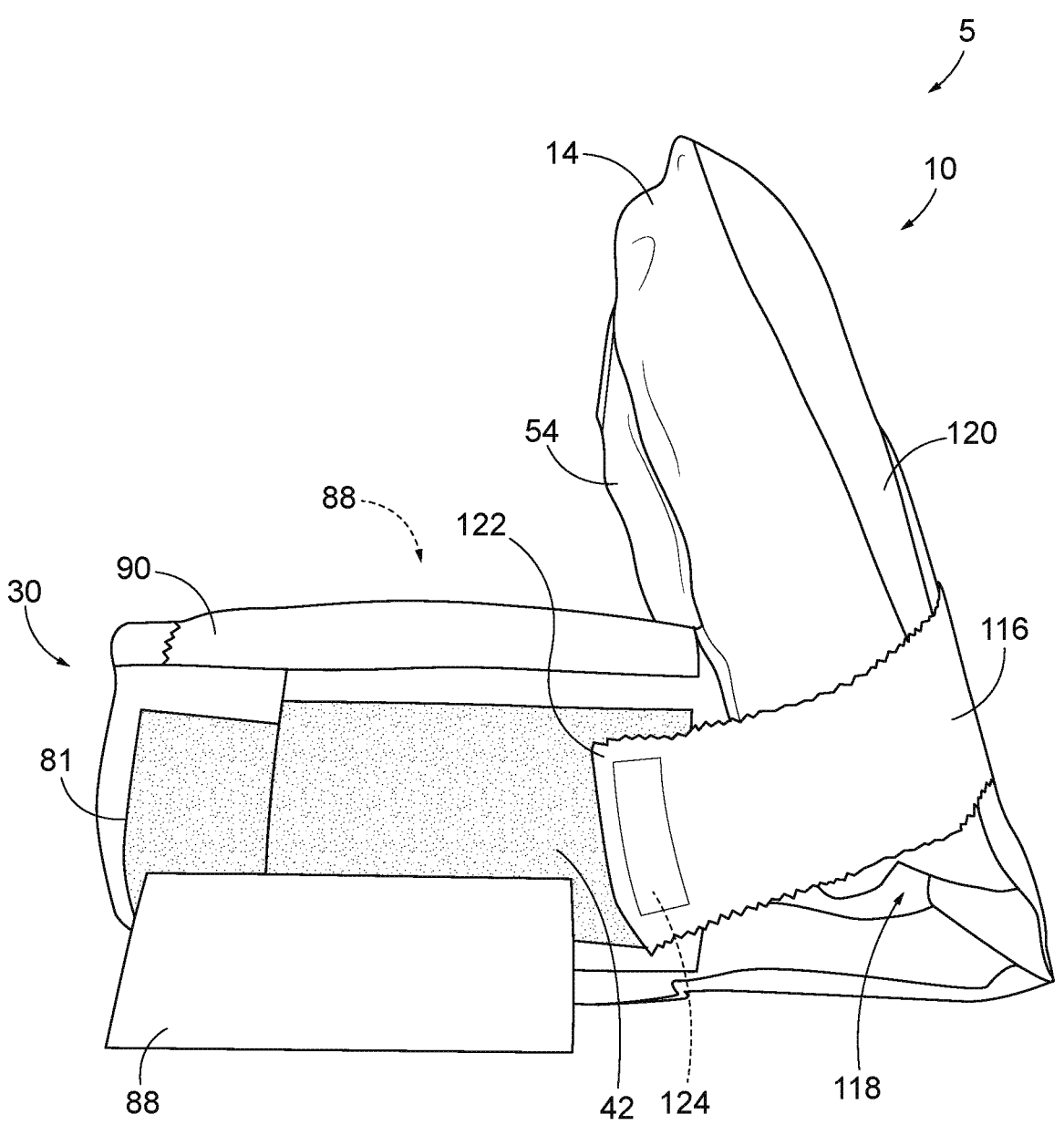
FIG. 13 is a side elevation view of the heel offloading device and lower extremity orthosis system of FIG. 12.

FIGS. 12-13 illustrate an additional example of system 5, showing an example of heel offloading device 30 selectively releasably secured to lower extremity orthosis 10, shown from a bottom perspective view (FIG. 12) and a side elevation view (FIG. 13). In FIG. 12, an example of stabilizing structure 88 is shown spaced apart from heel offloading device 30 for illustrative purposes, and in FIG. 13, stabilizing structure 88 is shown positioned against heel offloading device 30. Systems 5 may include additional stabilizing structures 88, such as another stabilizing structure 88 positioned on the other side of heel offloading device 30. For example, systems 5 may include at least one stabilizing structure 88 on a medial side of heel offloading device 30 and/or at least one stabilizing structure 88 on a lateral side of heel offloading device 30, with the side corresponding to the medial or lateral side of heel offloading device 30 depending on which leg system 5 is being used on. In other words, if system 5 were placed on a patient's right leg in the view of FIG. 13, the visible stabilizing structure 88 would be on the lateral side of heel offloading device 30, whereas if system 5 were placed on a patient's left leg in the view of FIG. 13, the visible stabilizing structure 88 would be on the medial side of heel offloading device 30.

As best seen in FIG. 12, stabilizing structure 88 may include hook and loop fasteners 112 on one or more sides, surfaces, or edges, or contours to engage with heel offloading device 30 (e.g., via hook and loop fasteners 42 on heel offloading device 30). For example, stabilizing structure 88 of FIG. 12 includes hook and loop fasteners covering substantially all of a first face 114, with said first face 114 being configured to contact heel offloading device 30 when stabilizing structure 88 is in use. Other surfaces of stabilizing structure 88 may be free from hook and loop fasteners. In various examples of stabilizing structure 88, some or all of one or more faces of stabilizing structure 88 may include hook and loop fasteners 112. While hook and loop fasteners 112 are shown in FIG. 12 as substantially covering first face 114, in other examples hook and loop fasteners 112 may be present only in discrete areas, such as in rows, strips, corners, edges, dots, squares, and/or any desired configuration sufficient to create the desired connection between stabilizing structure 88 and heel offloading device 30. Of course, stabilizing structure 88 may be engaged with heel offloading device 30 via friction, releasable adhesive, magnets, and/or any other releasable fastening method, or stabilizing structure 88 may simply be positioned with respect to heel offloading device 30 without any additional securement to heel offloading device 30. While stabilizing structure 88 is shown as a triangular prism in FIGS. 12-13, many different shapes and configurations may be appropriate for stabilizing structure 88, including but not limited to wedges, rectangular prisms, cubes, and/or any other shape or form that is resistant to rolling away from heel offloading device 30. Stabilizing structures 88 may be formed of any desired materials, including but not limited to foam, plastics, metallic materials, rubbers, or even wood or cardboard based materials. Stabilizing structures 88 may be configured to be disposable, single-use structures, or may be configured to be suitable for cleaning and sterilization such that they may be configured for multiple uses.

FIGS. 12-13 illustrate cover 90 secured across heel offloading device 30 and elastic member 54 secured across lower extremity orthosis 10, as if system 5 were being worn on a patient's lower leg and foot. Cover 90 generally helps to prevent heel offloading device 30 from accidental removal from the patient's lower leg, and elastic member 54 generally helps to keep the patient's foot within foot engagement portion 14 of lower extremity orthosis 10. Additionally or alternatively, one or more securement straps 116 may be provided to help secure the position of lower extremity orthosis 10 with respect to heel offloading device 30. In some examples, securement strap 116 may extend around an outer surface 120 of foot engagement portion 14, such that opposing end regions 122 of securement strap 116 may be selectively releasably secured to heel offloading device 30. For example, each opposing end region 122 of securement strap 116 may include an area of hook and loop fasteners 124 which may be configured to selectively releasably secure the respective opposing end region 122 to heel offloading device 30 (e.g., via hook and loop fasteners 42 of heel offloading device 30). As with cover 90 and elastic member 54, securement strap 116 may be formed of elastic material, though the function of securement strap 116 may be provided by a strap, belt, covering, webbing, or other fabric or textile that may not necessarily be elastic, but is generally flexible and comfortable to be secured against the top of the patient's foot. Securement strap 116 may be configured to secure lower extremity orthosis 10 to heel offloading device 30, such as to prevent or reduce translation of elongated positioning member 16 away from heel offloading device 30. Additionally or alternatively, securement strap 116 may be configured to urge foot engagement portion 14 towards heel offloading device 30 to facilitate correct positioning of the patient's foot with respect to the patient's leg. Systems 5 advantageously may be configured to create a gap, or space 118 (FIG. 13) such that the patients heel does not contact lower extremity orthosis 10 when worn.

In some examples, securement strap 116 may be a strap that simply wraps around foot engagement portion 14 and heel offloading device 30 similar to the way a flexible bandage wrap may be stretched and wrapped (e.g., an Ace® Bandage). In some examples, securement strap 116 may be sewn or otherwise coupled to foot engagement portion 14, with one or both opposing end regions 122 being loose when not secured to heel offloading device 30 via hook and loop fasteners 124, 42. For example, securement strap 116 may be sewn or otherwise coupled to foot engagement portion 14, such as along one or more seams along outer surface 120, as will be understood by those of ordinary skill in the art. In alternative embodiments, one or both opposing end regions 122 may be secured to heel offloading device 30, while securement strap 116 may be a two-piece strap with other ends releasably secured to foot engagement portion 14. In other examples, securement strap 116 may be applied around foot engagement portion 14 using belt loops or other placement features to retain securement strap 116 against foot engagement portion 14 during use.

As examples of systems 5 are described herein, reference is made generally to "hook and loop fasteners." As the term is used, it is intended to indicate that one instance of "hook and loop fasteners" may comprises an area of hooks, and another instance of "hook and loop fasteners" may comprise an area of loops. In this manner, one area of "hook and loop fasteners" may be configured to be releasably secured to a corresponding area of "hook and loop fasteners" of the opposite type, as is well understood in the art. The present disclosure is not limited in terms of whether hooks are present in one specific location or loops are present in another specific location, and it is within the scope of the present disclosure that the relative positions may be interchangeable in various examples of system 5. For example, in the example of FIG. 9, where hook and loop fasteners 42 are used to secure heel offloading device 30 to hook and loop fasteners 40 on upper surface 58 of sleeve 44, in one instance such hook and loop fasteners 42 may comprise hooks, and such hook and loop fasteners 40 may comprise loops, whereas in another instance such hook and loop fasteners 42 may comprise loops, and such hook and loop fasteners 40 may comprise hooks. Hook and loop fasteners 40, 42 may be any desired size and shape of said respective corresponding fasteners, such as rows, buttons, arrays, strips, and/or larger areas of such fasteners.

Figure 11:
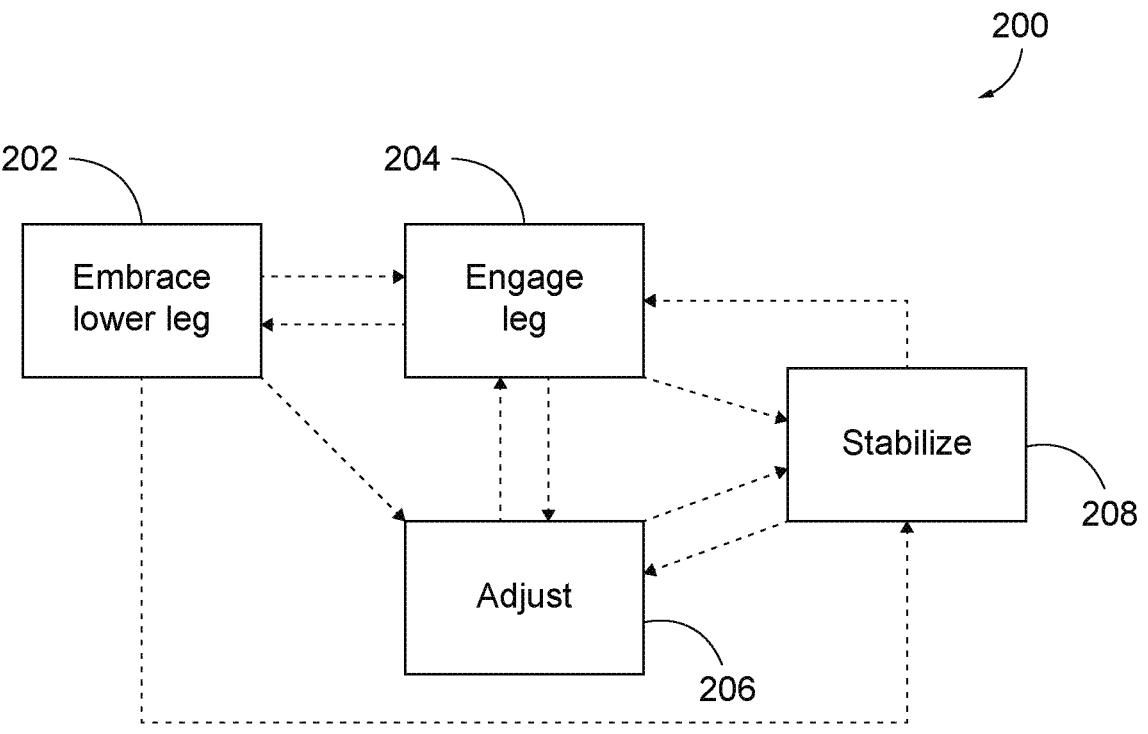
FIG. 11 is a schematic flowchart diagram illustrating methods according to the present disclosure.

FIG. 11 schematically provides a flowchart that represents illustrative, non-exclusive examples of methods 200 according to the present disclosure. In FIG. 11, some steps are illustrated in dashed boxes indicating that such steps may be optional or may correspond to an optional version of a method according to the present disclosure. That said, not all methods 200 according to the present disclosure are required to include the steps illustrated in solid boxes. The methods 200 and steps illustrated in FIG. 11 are not limiting and other methods and steps are within the scope of the present disclosure, including methods having greater than or fewer than the number of steps illustrated, as understood from the discussions herein.

Generally speaking, methods 200 may include embracing a patient's lower leg with a heel offloading device (e.g., heel offloading device 30) at 202 and engaging a lower extremity orthosis (e.g., lower extremity orthosis 10) with the heel offloading device at 204 to support the patient's foot relative to the heel offloading device. Embracing the patient's lower leg at 202 is performed using a heel offloading device that prevents the patient's heel from contacting a surface on which the patient is positioned (e.g., a bed, cot, floor, or other supporting surface). Engaging the lower extremity orthosis with the heel offloading device at 204 is performed using a lower extremity orthosis designed to prevent or reduce plantar flexion of the patient's foot while the patient's lower leg is embraced in the heel offloading device.

In some methods 200, engaging the lower extremity orthosis at 204 involves coupling the lower extremity orthosis to the heel offloading device via engagement between a lower leg-underlying portion of the lower extremity orthosis (e.g., lower leg-underlying portion 26) and an outer surface of the heel offloading device. For example, the lower leg-underlying portion of the lower extremity orthosis may be engaged with a form-fitting shell (e.g., form-fitting shell 82) enclosing or surrounding a concave member (thereby forming the outer surface of the heel offloading device). In other examples, the lower leg-underlying portion of the lower extremity orthosis may be engaged with the external surface of the concave member of the heel offloading device (e.g., directly engaged with external surface 94). Additionally or alternatively, engaging the lower extremity orthosis at 204 may involve coupling a sleeve of the lower leg-underlying portion of the lower extremity orthosis (e.g., sleeve 44 positioned on elongated positioning member 16) to the heel offloading device. Additionally or alternatively, engaging the lower extremity orthosis at 204 may include at least partially inserting the lower leg-underlying portion of the lower extremity orthosis into a slot or pocket of the heel offloading device (e.g., pocket 46), thereby selectively and releasably coupling the lower extremity orthosis to the heel offloading device.

Embracing the lower leg at 202 may include extending a cover (e.g., cover 90) between first and second sidewalls (e.g., sidewalls 70, 72) of the heel offloading device to provide a snug fit with lateral regions of the patient's lower leg, and/or reversibly coupling the cover to the heel offloading device. Some methods 200 may include adjusting the heel offloading device and/or the lower extremity orthosis, at 206, to accommodate variations in patient size and/or desired positioning or comfort. For example, adjusting the system at 206 may include selectively translating a foot engagement portion of the lower extremity orthosis (e.g., foot engagement portion 14) with respect to a foot-underlying portion of the elongated positioning member of the lower extremity orthosis (e.g., foot-underlying portion 24). Additionally or alternatively, adjusting the system at 206 may include selectively adjusting an overall length of the lower extremity orthosis via selective translation of the lower leg-underlying portion of the elongated positioning member of the lower extremity orthosis with respect to the heel offloading device. Additionally or alternatively, adjusting the system at 206 may include selectively shortening the elongated positioning member of the lower extremity orthosis.

Methods 200 may include stabilizing the heel offloading device and/or lower extremity orthosis about a surface below the heel offloading device, at 208. For example, stabilizing the heel offloading device at 208 may include placing a stabilizing structure (e.g., stabilizing structure 88) such that it is wedged against the heel offloading device and/or against the lower extremity orthosis, thereby stabilizing one or both. Additionally or alternatively, stabilizing the heel offloading device at 208 may include coupling one or more stabilizing structures to the heel offloading device and/or to the lower extremity orthosis, such as via hook and loop fasteners, or other releasable fastening means.

Illustrative, non-exclusive examples of inventive subject matter according to the present disclosure are described in the following enumerated paragraphs:

A1. A lower extremity orthosis, comprising:
a foot engagement portion configured to engage a patient's foot, the foot engagement portion comprising opposing sidewalls extending from a sole-supporting surface configured to engage with a sole of the patient's foot; and an elongated positioning member comprising a foot-underlying portion and a lower leg-underlying portion, wherein the foot-underlying portion of the elongated positioning member is configured to couple the elongated positioning member to the foot engagement portion, wherein the lower extremity orthosis is configured to be selectively and removably engaged with a heel offloading device via the lower leg-underlying portion of the elongated positioning member, such that the lower extremity orthosis is configured to prevent or reduce plantar flexion when the heel offloading device is used and the lower extremity orthosis is applied to the patient's foot.

A1.1. The lower extremity orthosis of paragraph A1, wherein the foot-underlying portion of the elongated positioning member is configured to underlie the patient's foot when the lower extremity orthosis is applied to the patient's foot, and wherein the lower leg-underlying portion of the elongated positioning member is configured to underlie the patient's lower leg when the lower extremity orthosis is applied to the patient's foot.

A2. The lower extremity orthosis of paragraph A1 or A1.1, wherein the foot-underlying portion of the elongated positioning member is arranged at a non-parallel angle with respect to the lower leg-underlying portion of the elongated positioning member.

A2.1. The lower extremity orthosis of paragraph A2, wherein the non-parallel angle is less than 70 degrees, less than 75 degrees, less than 80 degrees, less than 85 degrees, less than 90 degrees, less than 95 degrees, less than 100 degrees, less than 105 degrees, and/or less than 110 degrees.

A2.2. The lower extremity orthosis of paragraph A2 or A2.1, wherein the non-parallel angle is substantially fixed.

A2.3. The lower extremity orthosis of paragraph A2 or A2.1, wherein the non-parallel angle is selectively adjustable.

A3. The lower extremity orthosis of any of paragraphs A1-A2.3, wherein the elongated positioning member is configured to couple the lower extremity orthosis to the heel offloading device such that the foot engagement portion maintains a threshold angle with respect to a longitudinal axis of the heel offloading device, thereby preventing or reducing plantar flexion of the patient's foot.

A4. The lower extremity orthosis of paragraph A3, wherein the threshold angle is less than 70 degrees, less than 75 degrees, less than 80 degrees, less than 85 degrees, less than 90 degrees, less than 95 degrees, less than 100 degrees, less than 105 degrees, and/or less than 110 degrees.

A4.1. The lower extremity orthosis of paragraph A3 or A4, wherein the threshold angle is selectively adjustable.

A5. The lower extremity orthosis of any of paragraphs A1-A4.1, wherein the lower leg-underlying portion is configured to couple the lower extremity orthosis to the heel offloading device via engagement with an outer surface of the heel offloading device.

A6. The lower extremity orthosis of any of paragraphs A1-A5, wherein the lower leg-underlying portion comprises a first hook and loop fastener configured to couple the lower extremity orthosis to the heel offloading device via engagement with a second hook and loop fastener of the heel offloading device.

A7. The lower extremity orthosis of any of paragraphs A1-A6, wherein the lower leg-underlying portion comprises a sleeve configured to selectively and removably couple the lower extremity orthosis to the heel offloading device.

A7.1. The lower extremity orthosis of paragraph A7, wherein the sleeve comprises a/the first hook and loop fastener.

A7.2. The lower extremity orthosis of paragraph A7 or A7.1, wherein the sleeve comprises a fastener configured to selectively and removably couple the lower extremity orthosis to the heel offloading device.

A8. The lower extremity orthosis of any of paragraphs A1-A7.2, wherein the lower leg-underlying portion is configured to be at least partially inserted into a slot or pocket of the heel offloading device to couple the lower extremity orthosis to the heel offloading device.

A9. The lower extremity orthosis of any of paragraphs A1-A8, wherein the elongated positioning member is selectively removable from the foot engagement portion.

A10. The lower extremity orthosis of any of paragraphs A1-A9, wherein the foot engagement portion is selectively translatable with respect to the foot-underlying portion of the elongated positioning member.

A11. The lower extremity orthosis of any of paragraphs A1-A10, wherein the lower extremity orthosis is configured to be selectively adjustable in overall length via selective translation of the lower leg-underlying portion of the elongated positioning member with respect to the heel offloading device.

A12. The lower extremity orthosis of any of paragraphs A1-A11, wherein the foot engagement portion defines a cavity configured to receive the patient's foot without enclosing the patient's foot.

A13. The lower extremity orthosis of any of paragraphs A1-A12, wherein the foot engagement portion comprises an elastic member configured to secure the patient's foot within a/the cavity of the foot engagement portion.

A14. The lower extremity orthosis of paragraph A13, wherein the elastic member comprises one or more elastic straps, one or more elastic bands, and/or one or more elastic coverings that extend transversely and/or angularly across the cavity of the foot engagement portion.

A15. The lower extremity orthosis of paragraph A13 or A14, wherein the elastic member is fixedly secured to the foot engagement portion.

A16. The lower extremity orthosis of any of paragraphs A13-A15, wherein the elastic member is releasably secured to the foot engagement portion.

A17. The lower extremity orthosis of any of paragraphs A13-A16, wherein a tension of the elastic member is selectively adjustable.

A18. The lower extremity orthosis of any of paragraphs A1-A17, wherein the foot-underlying portion of the elongated positioning member is configured to be at least partially inserted into the foot engagement portion.

A19. The lower extremity orthosis of any of paragraphs A1-A18, wherein a lower surface of the lower leg-underlying portion of the elongated positioning member is configured to engage with the foot engagement portion.

A20. The lower extremity orthosis of any of paragraphs A1-A19, wherein an upper surface of the lower leg-underlying portion of the elongated positioning member is configured to engage with the heel offloading device.

A21. The lower extremity orthosis of any of paragraphs A1-A20, wherein the foot engagement portion is cushioned.

A21.1. The lower extremity orthosis of any of paragraphs A1-A21, wherein the foot engagement portion comprises foam, fiberfill, air, gel, padding, memory foam, and/or other cushioning materials.

A21.2. The lower extremity orthosis of any of paragraphs A1-A21.1, wherein the foot engagement portion comprises one or more bladders, which may be selectively or permanently filled, such as with air, water, gel, and/or other fluids A22. The lower extremity orthosis of any of paragraphs A1-A21.2, wherein the lower extremity orthosis is configured for use by patients who are bedridden, on bedrest, and/or in a supine or partially supine position.

A23. The lower extremity orthosis of any of paragraphs A1-A22, wherein the foot-underlying portion of the elongated positioning member is substantially perpendicular to the lower leg-underlying portion of the elongated positioning member.

A24. The lower extremity orthosis of any of paragraphs A1-A23, wherein the foot-underlying portion of the elongated positioning member is integrally formed with the lower leg-underlying portion of the elongated positioning member.

A25. The lower extremity orthosis of any of paragraphs A1-A24, wherein the elongated positioning member is rigid or semi-rigid.

A26. The lower extremity orthosis of any of paragraphs A1-A25, wherein the elongated positioning member comprises a curved heel portion positioned between the foot-underlying portion and the lower leg-underlying portion.

A27. The lower extremity orthosis of paragraph A26, wherein the curved heel portion is configured to avoid contacting the patient's heel when the lower extremity orthosis is used by the patient.

A28. The lower extremity orthosis of any of paragraphs A1-A27, wherein the lower extremity orthosis is configured to support the patient's lower leg, heel, and foot.

A29. The lower extremity orthosis of any of paragraphs A1-A28, wherein the lower extremity orthosis is configured to be customized for different sizes of patients.

A30. The lower extremity orthosis of any of paragraphs A1-A29, wherein the elongated positioning member comprises one or more score lines such that a length of the elongated positioning member may be selectively reduced by shortening the elongated positioning member at the score line.

A31. The lower extremity orthosis of any of paragraphs A1-A30, further comprising a securement strap sewn to an outer surface of the foot engagement portion, wherein the securement strap extends from the outer surface to a first and second opposing end region, wherein the first and second opposing end regions are configured to selectively releasably engage the heel offloading device.

B1. A system, comprising:
the lower extremity orthosis of any of paragraphs A1-A31; and
the heel offloading device.

B2. The system of paragraph B1, wherein the lower extremity orthosis is selectively and removably engaged with the heel offloading device via the lower leg-underlying portion of the elongated positioning member of the lower extremity orthosis, such that the lower extremity orthosis is configured to prevent or reduce plantar flexion when the heel offloading device is used and the lower extremity orthosis is applied to the patient's foot.

B3. The system of any of paragraphs B1-B2, wherein the elongated positioning member couples the lower extremity orthosis to the heel offloading device such that the foot engagement portion maintains a threshold angle with respect to a longitudinal axis of the heel offloading device, thereby preventing or reducing plantar flexion of the patient's foot.

B4. The system of paragraph B3, wherein the threshold angle is less than 70 degrees, less than 75 degrees, less than 80 degrees, less than 85 degrees, less than 90 degrees, less than 95 degrees, less than 100 degrees, less than 105 degrees, and/or less than 110 degrees.

B5. The system of paragraph B3 or B4, wherein the threshold angle is selectively adjustable.

B6. The system of any of paragraphs B1-B5, wherein the lower leg-underlying portion couples the lower extremity orthosis to the heel offloading device via engagement with an/the outer surface of the heel offloading device.

B7. The system of any of paragraphs B1-B6, wherein the lower leg-underlying portion comprises a/the first hook and loop fastener that couples the lower extremity orthosis to the heel offloading device via engagement with a/the second hook and loop fastener of the heel offloading device.

B8. The system of any of paragraphs B1-B7, wherein the lower leg-underlying portion comprises a/the sleeve that selectively and removably couples the lower extremity orthosis to the heel offloading device.

B9. The system of paragraph B8, wherein the sleeve comprises a/the first hook and loop fastener.

B10. The system of paragraph B8 or B9, wherein the sleeve comprises a/the fastener that selectively and removably couples the lower extremity orthosis to the heel offloading device.

B11. The system of any of paragraphs B1-B10, wherein the lower leg-underlying portion is at least partially inserted into a/the slot or pocket of the heel offloading device to couple the lower extremity orthosis to the heel offloading device.

B12. The system of any of paragraphs B1-B11, wherein the lower extremity orthosis is selectively adjustable in overall length via selective translation of the lower leg-underlying portion of the elongated positioning member with respect to the heel offloading device.

B13. The system of any of paragraphs B1-B12, wherein an upper surface of the lower leg-underlying portion of the elongated positioning member is engaged with the heel offloading device.

B14. The system of any of paragraphs B1-B13, wherein the heel offloading device comprises:
a concave member extending from a first end to a second end, the first end being configured to engage the patient's lower leg superior to the patient's ankle, and the second end being configured to engage the lower leg at or inferior to the patient's mid-calf.

B15. The system of any of paragraphs B1-B14, wherein the heel offloading device comprises:
a first and second sidewall projecting from a floor of a/the concave member, wherein interior portions of the first and second sidewalls and the floor together define a lower leg-receiving surface that is configured to embrace the patient's lower leg when the heel offloading device is worn by the patient.

B16. The system of paragraph B15, wherein the first and second sidewalls are tapered to be thicker about the first end of the concave member in at least one cross section, and thinner about the second end of the concave member in at least another cross section.

B17. The system of any of paragraphs B1-B16, wherein a/the floor of the heel offloading device defines at least three levels of thickness in relation to a base of the heel offloading device, each of the three levels being different from any of the other three levels.

B17.1. The system of paragraph B17, wherein one of the three levels extends from a/the first end of a/the concave member and another of the three levels extends from a/the second end of the concave member, wherein the thickness of the one level is greater than the other level.

B17.2. The system of paragraph B17 or B17.1, wherein the thickest of the three levels extends about midway between a/the first and second ends of a/the concave member with the other levels bracketing the thickest levels and being thinner than the thickest levels.

B18. The system of any of paragraphs B1-B17.2, wherein the heel offloading device comprises a cell foam material.

B18.1. The system of any of paragraphs B1-B18, wherein the heel offloading device comprises one or more bladders, which may be selectively or permanently filled, such as with air, water, gel, and/or other fluids.

B19. The system of any of paragraphs B1-B18.1, wherein the heel offloading device comprises a form-fitting shell at least partially enclosing a/the concave member of the heel offloading device.

B20. The system of any of paragraphs B1-B19, wherein the heel offloading device comprises a releasable material extending along at least a portion of a length of a/the concave member of the heel offloading device and/or along at least a portion of a/the form-fitting shell of the heel offloading device.

B21. The system of any of paragraphs B1-B20, further comprising a stabilizing structure configured to be selectively releasably coupled to the heel offloading device.

B22. The system of any of paragraphs B1-B21, wherein the heel offloading device further comprises a cover extending between portions of a/the form-fitting shell, along at least a portion of a/the length of a/the concave member of the heel offloading device, and/or transversely across a/the floor of the heel offloading device, between a/the first and second sidewalls.

B23. The system of paragraph B22, wherein the cover is coupled to one of the first sidewall and the second sidewall, and wherein the cover is selectively releasably securable to the other of the first sidewall and the second sidewall.

B24. The system of paragraph B22 or B23, wherein the heel offloading device comprises the form-fitting shell, and wherein the form-fitting shell includes the cover.

B25. The system of any of paragraphs B22-B24, wherein the cover is configured to cover and/or extend across at least a portion of the patient's shin when the heel offloading device is worn by the patient, and wherein the cover is configured to prevent accidental or unintentional removal of the heel offloading device from the patient's lower leg.

B26. The system of any of paragraphs B1-B25, wherein a/the concave member of the heel offloading device defines a substantially U-shape in at least one cross section.

B27. The system of any of paragraphs B1-B26, wherein a/the first and second sidewall of a/the concave member of the heel offloading device are substantially pliable.

C1. A method, comprising:

embracing a patient's lower leg with a heel offloading device such that the patient's heel is prevented from contacting a surface on which the patient is positioned; and engaging a lower extremity orthosis with the heel offloading device such that the lower extremity orthosis is configured to reduce or prevent plantar flexion of the patient's foot.

C2. The method of paragraph C1, wherein the lower extremity orthosis comprises the lower extremity orthosis of any of paragraphs A1-A31.

C3. The method of paragraph C1 or C2, wherein the heel offloading device is the heel offloading device as described in the system of any of paragraphs B1-B27.

C4. The method of any of paragraphs C1-C3, wherein the engaging the lower extremity orthosis comprises coupling the lower extremity orthosis to the heel offloading device via engagement between a/the lower leg-underlying portion of the lower extremity orthosis and an/the outer surface of the heel offloading device.

C5. The method of any of paragraphs C1-C4, wherein the engaging the lower extremity orthosis comprises coupling a/the sleeve of a/the lower leg-underlying portion of the lower extremity orthosis to the heel offloading device.

C6. The method of any of paragraphs C1-C5, wherein the engaging the lower extremity orthosis comprises at least partially inserting a/the lower leg-underlying portion of the lower extremity orthosis into a/the slot or pocket of the heel offloading device, thereby selectively and releasably coupling the lower extremity orthosis to the heel offloading device.

C7. The method of any of paragraphs C1-C6, further comprising selectively translating a/the foot engagement portion of the lower extremity orthosis with respect to a/the foot-underlying portion of a/the elongated positioning member of the lower extremity orthosis.

C8. The method of any of paragraphs C1-C7, further comprising selectively adjusting an/the overall length of the lower extremity orthosis via selective translation of a/the lower leg-underlying portion of a/the elongated positioning member of the lower extremity orthosis with respect to the heel offloading device.

C9. The method of any of paragraphs C1-C8, further comprising selectively shortening a/the elongated positioning member of the lower extremity orthosis.

C10. The method of any of paragraphs C1-C9, further comprising stabilizing the heel offloading device about a surface below the heel offloading device.

C11. The method of any of paragraphs C1-C10, further comprising reversibly coupling a/the stabilizing structure to the heel offloading device.

C12. The method of any of paragraphs C1-C11, further comprising extending a/the cover between a/the first and second sidewalls of the heel offloading device to provide a snug fit with lateral regions of the patient's lower leg.

C13. The method of any of paragraphs C1-C12, further comprising reversibly coupling a/the cover to the heel offloading device.

D1. The use of the lower extremity orthosis of any of paragraphs A1-A31 to prevent plantar flexion and/or prevent pressure ulcers in the patient's foot.

D2. The use of the system of any of paragraphs B1-B27 to prevent plantar flexion and/or prevent pressure ulcers in the patient's foot.

E1. A system, comprising:

a lower extremity orthosis, comprising:

a foot engagement portion configured to engage a patient's foot, the foot engagement portion comprising opposing sidewalls extending from a sole-supporting surface configured to engage with a sole of the patient's foot, wherein the foot engagement portion defines a cavity configured to receive the patient's foot without enclosing the patient's foot; and an elongated positioning member comprising a foot-underlying portion and a lower leg-underlying portion, wherein the foot-underlying portion of the elongated positioning member is configured to couple the elongated positioning member to the foot engagement portion, wherein the elongated positioning member is configured to couple the lower extremity orthosis to the heel offloading device such that the foot engagement portion maintains a threshold angle with respect to a longitudinal axis of the heel offloading device, thereby preventing or reducing plantar flexion of the patient's foot, wherein the lower extremity orthosis is configured to be selectively and removably engaged with a heel offloading device via the lower leg-underlying portion of the elongated positioning member, such that the lower extremity orthosis is configured to prevent or reduce plantar flexion when the heel offloading device is used and the lower extremity orthosis is applied to the patient's foot, wherein the lower extremity orthosis is configured to be selectively adjustable in overall length via selective translation of the lower leg-underlying portion of the elongated positioning member with respect to the heel offloading device; and the heel offloading device, wherein the heel offloading device comprises:

a concave member extending from a first end to a second end, the first end being configured to engage the patient's lower leg superior to the patient's ankle such that the patient's foot and ankle are free from restraint by the concave member, and the second end being configured to engage the lower leg at or inferior to the patient's mid-calf; and a first and second sidewall projecting from a floor of the concave member, wherein interior portions of the first and second sidewalls and the floor together define a lower leg-receiving surface that is configured to embrace the patient's lower leg when the heel offloading device is worn by the patient, wherein the first and second sidewalls are tapered to be thicker about the first end of the concave member in at least one cross section, and thinner about the second end of the concave member in at least another cross section.

As used herein, the terms "selective" and "selectively," when modifying an action, movement, configuration, or other activity of one or more components or characteristics of an apparatus, mean that the specific action, movement, configuration, or other activity is a direct or indirect result of dynamic processes and/or user manipulation of an aspect of, or one or more components of, the apparatus. The terms "selective" and "selectively" thus may characterize an activity that is a direct or indirect result of user manipulation of an aspect of, or one or more components of, the apparatus, or may characterize a process that occurs automatically, such as via the mechanisms disclosed herein.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the phrase "at least one," in reference to a list of one or more entities should be understood to mean at least one entity selected from any one or more of the entities in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one example, to at least one, optionally including more than one, A, with no B present (and optionally including entities other than B); in another example, to at least one, optionally including more than one, B, with no A present (and optionally including entities other than A); in yet another example, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C" and "A, B, and/or C" may mean A alone, B alone, C alone, A and B together, A and C together, B and C together, or A, B, and C together, and optionally any of the above in combination with at least one other entity.

As used herein, the phrase "at least substantially," when modifying a degree or relationship, includes not only the recited "substantial" degree or relationship, but also the full extent of the recited degree or relationship. A substantial amount of a recited degree or relationship may include at least 75% of the recited degree or relationship. For example, a first direction that is at least substantially parallel to a second direction includes a first direction that is within an angular deviation of 22.5° relative to the second direction and also includes a first direction that is identical to the second direction.

The various disclosed elements of apparatuses and steps of methods disclosed herein are not required to all apparatuses and methods according to the present disclosure, and the present disclosure includes all novel and non-obvious combinations and subcombinations of the various elements and steps disclosed herein. Moreover, one or more of the various elements and steps disclosed herein may define independent inventive subject matter that is separate and apart from the whole of a disclosed apparatus or method. Accordingly, such inventive subject matter is not required to be associated with the specific apparatuses and methods that are expressly disclosed herein, and such inventive subject matter may find utility in apparatuses and/or methods that are not expressly disclosed herein.

As used herein, the phrase, "for example," the phrase, "as an example," and/or simply the term "example," when used with reference to one or more components, features, details, structures, examples, and/or methods according to the present disclosure, are intended to convey that the described component, feature, detail, structure, example, and/or method is an illustrative, non-exclusive example of components, features, details, structures, examples, and/or methods according to the present disclosure. Thus, the described component, feature, detail, structure, example, and/or method is not intended to be limiting, required, or exclusive/exhaustive; and other components, features, details, structures, examples, and/or methods, including structurally and/or functionally similar and/or equivalent components, features, details, structures, examples, and/or methods, are also within the scope of the present disclosure.

The invention claimed is:

1. A method of preventing plantar flexion comprising:
providing a lower extremity orthosis comprising;
a foot engagement portion configured to engage a foot of a patient, the foot engagement portion comprising opposing pliable sidewalls extending from a sole-supporting surface and defining a cavity configured to receive the foot without enclosing the foot, and an elastic member configured to span across an open top of the cavity to bias the opposing sidewalls toward one another when secured, the elastic member being selectively releasable from at least one of the opposing sidewalls; and
an elongated positioning member comprising a foot-underlying portion and a lower leg-underlying portion joined by a curved heel portion sized and shaped to avoid contacting a heel of the patient when the orthosis is worn, the foot-underlying portion being contained within or secured to the foot engagement portion to couple the elongated positioning member to the foot engagement portion,
wherein the lower leg-underlying portion is configured to selectively and removably couple the lower extremity orthosis to a heel offloading device external to the foot engagement portion via at least one of: (i) at least partial insertion of the lower leg-underlying portion into a slot or pocket of the heel offloading device; and (ii) engagement between a sleeve disposed around the lower leg-underlying portion and a releasable material on an outer surface of the heel offloading device,
wherein, when the lower extremity orthosis is coupled to the heel offloading device, the elongated positioning member positions the foot engagement portion to maintain a threshold angle with respect to a longitudinal axis of the heel offloading device that is less than 95°, thereby preventing or reducing plantar flexion of the foot while the heel offloading device is used and the lower extremity orthosis is applied to the foot, and
further wherein a space between the foot engagement portion and the lower leg-underlying portion remains open laterally and anteriorly such that, when the device is worn, the heel of the patient is externally visible and accessible for clinical care through the open cavity and lateral regions of the foot engagement portion; and
securing the lower extremity orthosis device to a lower extremity of the patient to offload the heel of the patient.

2. The method of preventing plantar flexion of claim 1 further comprising removing at least one of the foot engagement portion and the lower leg engagement portion to expose the elongated positioning member.

3. The method of preventing plantar flexion of claim 2 wherein the elongated positioning member further comprises one or more score lines operable to selectively shorten the length of the elongated positioning member further comprising the step of bending the elongated positioning member along a score line of the one or more score lines.

4. The method of preventing plantar flexion of claim 3 further comprising securing the removed at least one of the foot engagement portion and the lower leg engagement portion to the elongated positioning member.

5. A lower extremity orthosis device for a patient comprising:
a foot engagement portion configured to engage a foot of a patient, the foot engagement portion comprising opposing pliable sidewalls extending from a sole-supporting surface and defining a cavity configured to receive the foot without enclosing the foot, and an elastic member configured to span across an open top of the cavity to bias the opposing sidewalls toward one another when secured, the elastic member being selectively releasable from at least one of the opposing sidewalls; and
an elongated positioning member comprising a foot-underlying portion and a lower leg-underlying portion joined by a curved heel portion sized and shaped to avoid contacting a heel of the patient when the orthosis is worn, the foot-underlying portion being contained within or secured to the foot engagement portion to couple the elongated positioning member to the foot engagement portion,
wherein the lower leg-underlying portion is configured to selectively and removably couple the lower extremity orthosis to a heel offloading device external to the foot engagement portion via at least one of: (i) at least partial insertion of the lower leg-underlying portion into a slot or pocket of the heel offloading device; and (ii) engagement between a sleeve disposed around the lower leg-underlying portion and a releasable material on an outer surface of the heel offloading device,
wherein, when the lower extremity orthosis is coupled to the heel offloading device, the elongated positioning member positions the foot engagement portion to maintain a threshold angle with respect to a longitudinal axis of the heel offloading device that is less than 95°, thereby preventing or reducing plantar flexion of the foot while the heel offloading device is used and the lower extremity orthosis is applied to the foot, and
further wherein a space between the foot engagement portion and the lower leg-underlying portion remains open laterally and anteriorly such that, when the device is worn, the heel of the patient is externally visible and accessible for clinical care through the open cavity and lateral regions of the foot engagement portion.

6. The lower extremity orthosis device of claim 5 wherein the foot-engagement surface is arranged at a non-parallel angle with respect to the lower leg engagement portion of the elongated positioning member, and wherein the non-parallel angle is less 110 degrees.

7. The lower extremity orthosis device of claim 5 wherein the curved heel portion of the elongated positioning member maintains a threshold angle of the foot of the patient with respect to a longitudinal axis of the device.

8. The lower extremity orthosis device of claim 5 wherein the foot engagement portion and the lower leg engagement portion are padded.

9. The lower extremity orthosis device of claim 5 further comprising a sleeve operable to selectively and removably couple the lower extremity orthosis device to the lower leg engagement portion.

10. The lower extremity orthosis device of claim 5 wherein the foot engagement portion and the lower leg engagement portion are removable.

11. The lower extremity orthosis device of claim 5 wherein the lower leg engagement portion has a lower leg pocket operable to receive the second end of the elongated positioning member.

12. The lower extremity orthosis device of claim 5 wherein the foot engagement portion has a foot engagement pocket operable to receive the first end of the elongated positioning member.

13. The lower extremity orthosis device of claim 5 wherein the elongated positioning member further comprises one or more score lines operable to selectively shorten the length of the elongated positioning member.

14. The lower extremity orthosis device of claim 5 wherein the lower extremity orthosis device is configurable to be sized for the patient.

15. The lower extremity orthosis device of claim 5 wherein a floor of the device comprises at least three levels of thickness in relation to a base of the device.

16. The lower extremity orthosis device of claim 5 wherein at least one of the elastic member and the cover include a hook and loop fastener.

17. The lower extremity orthosis device of claim 5 wherein the foot engagement portion is releasably secured to the lower leg engagement portion.

\* \* \* \* \*